United States Patent
Daoud et al.

(10) Patent No.: US 9,503,526 B2
(45) Date of Patent: Nov. 22, 2016

(54) THERAPY MANAGEMENT SYSTEM

(75) Inventors: Saleem Daoud, San Diego, CA (US); Christopher Jung, San Diego, CA (US); Gregory Grant Haines, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 565 days.

(21) Appl. No.: 13/564,188

(22) Filed: Aug. 1, 2012

(65) Prior Publication Data

US 2013/0159456 A1 Jun. 20, 2013

Related U.S. Application Data

(60) Provisional application No. 61/513,998, filed on Aug. 1, 2011, provisional application No. 61/656,731, filed on Jun. 7, 2012.

(51) Int. Cl.
*G06F 19/00* (2011.01)
*H04L 29/08* (2006.01)
*H04L 29/06* (2006.01)

(52) U.S. Cl.
CPC ............ *H04L 67/12* (2013.01); *G06F 19/322* (2013.01); *G06F 19/3406* (2013.01); *G06F 19/3418* (2013.01); *G06F 19/3468* (2013.01); *H04L 63/10* (2013.01)

(58) Field of Classification Search
CPC . A61B 5/0022; G06F 19/34; G06F 19/3406; G06F 19/3418; G06F 19/3468; H04L 63/10
See application file for complete search history.

(56) References Cited

U.S. PATENT DOCUMENTS

| | | | |
|---|---|---|---|
| 5,429,602 A | * | 7/1995 | Hauser ............... A61M 5/1413 604/65 |
| 5,497,772 A | | 3/1996 | Schulman et al. |
| 5,660,163 A | | 8/1997 | Schulman et al. |
| 5,822,715 A | | 10/1998 | Worthington et al. |
| 6,024,699 A | | 2/2000 | Surwit et al. |
| 6,068,615 A | | 5/2000 | Brown et al. |
| 6,110,148 A | | 8/2000 | Brown et al. |
| 6,113,578 A | | 9/2000 | Brown |
| 6,270,455 B1 | | 8/2001 | Brown |
| 6,272,468 B1 | | 8/2001 | Melrose |
| 6,352,523 B1 | | 3/2002 | Brown et al. |
| 6,442,433 B1 | | 8/2002 | Linberg |
| 6,564,104 B2 | | 5/2003 | Nelson et al. |

(Continued)

OTHER PUBLICATIONS

Application No. PCT/US2012/049145, International Search Report, mailed Feb. 27, 2013, 5 pages.

(Continued)

*Primary Examiner* — Jeong S Park
(74) *Attorney, Agent, or Firm* — Patterson Thuente Pedersen, P.A.

(57) ABSTRACT

Stored data is accessed over a computer network through a network data manager. Data may be stored and transferred to the network data manager from a product device using an uploader application. In one aspect, a request message containing an access request or identifier is received at the network data manager from a client device for access to a data storage facility. If the network data manager determines the access requestor identifier is associated with a data record that identifies a product device having a registration record, the network data manager transmits a data link to the client device to provide access to the data record by the client device over the computer network.

30 Claims, 24 Drawing Sheets

(56) References Cited

U.S. PATENT DOCUMENTS

| | | |
|---|---|---|
| 6,649,403 B1 | 11/2003 | Mcdevitt et al. |
| 6,740,075 B2 | 5/2004 | Lebel et al. |
| 6,768,425 B2 | 7/2004 | Flaherty et al. |
| 6,958,691 B1 | 10/2005 | Anderson |
| 6,970,742 B2 | 11/2005 | Mann et al. |
| 7,025,743 B2 | 4/2006 | Mann et al. |
| 7,181,505 B2 | 2/2007 | Haller et al. |
| 7,316,899 B2 | 1/2008 | Mcdevitt et al. |
| 7,369,919 B2 | 5/2008 | Vonk et al. |
| 7,483,743 B2 | 1/2009 | Mann et al. |
| 7,647,237 B2 | 1/2010 | Malave et al. |
| 7,737,581 B2 | 6/2010 | Spurlin et al. |
| 7,779,183 B2 | 8/2010 | Koehler et al. |
| 7,877,489 B2 | 1/2011 | Salesky et al. |
| 7,942,844 B2 | 5/2011 | Moberg et al. |
| 7,963,946 B2 | 6/2011 | Moubayed et al. |
| 7,970,620 B2 | 6/2011 | Brown |
| 7,991,625 B2 | 8/2011 | Rosenfeld et al. |
| 7,996,245 B2 | 8/2011 | Gejdos et al. |
| 8,019,721 B2 | 9/2011 | Young et al. |
| 8,025,634 B1 | 9/2011 | Moubayed et al. |
| 8,106,534 B2 | 1/2012 | Spurlin et al. |
| 8,126,728 B2 | 2/2012 | Dicks |
| 8,126,729 B2 | 2/2012 | Dicks et al. |
| 8,126,730 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,140,356 B2 | 3/2012 | Dicks |
| 8,155,982 B2 | 4/2012 | Dicks et al. |
| 8,182,445 B2 | 5/2012 | Moubayed et al. |
| 8,211,364 B2 | 7/2012 | Drucker et al. |
| 8,249,894 B2 | 8/2012 | Brown |
| 8,257,652 B2 | 9/2012 | Drucker et al. |
| 8,257,653 B2 | 9/2012 | Drucker et al. |
| 8,313,433 B2 | 11/2012 | Cohen et al. |
| 8,348,885 B2 | 1/2013 | Moberg et al. |
| 8,398,592 B2 | 3/2013 | Leibner-Druska |
| 8,402,151 B2 | 3/2013 | Young et al. |
| 8,452,953 B2 | 5/2013 | Buck |
| 8,475,409 B2 | 7/2013 | Tsoukalis |
| 8,512,276 B2 | 8/2013 | Talbot et al. |
| 8,579,853 B2 | 11/2013 | Reggiardo et al. |
| 8,635,085 B2 | 1/2014 | Brown |
| 8,663,201 B2 | 3/2014 | Hill et al. |
| 8,952,794 B2 | 2/2015 | Blomquist |
| 8,971,958 B2 | 3/2015 | Frikart et al. |
| 2002/0029776 A1 | 3/2002 | Blomquist |
| 2002/0178126 A1 | 11/2002 | Beck |
| 2003/0208490 A1 | 11/2003 | Larrea |
| 2004/0235446 A1 | 11/2004 | Flaherty et al. |
| 2005/0091316 A1* | 4/2005 | Ponce ............... H04L 63/104 709/205 |
| 2005/0177395 A1 | 8/2005 | Blomquist |
| 2005/0246416 A1 | 11/2005 | Blomquist |
| 2006/0031094 A1 | 2/2006 | Cohen |
| 2006/0064143 A1* | 3/2006 | Von Arx ............ A61B 5/0031 607/60 |
| 2007/0060869 A1 | 3/2007 | Tolle et al. |
| 2007/0060870 A1 | 3/2007 | Tolle et al. |
| 2007/0093786 A1 | 4/2007 | Goldsmith et al. |
| 2007/0100222 A1 | 5/2007 | Mastrototaro et al. |
| 2007/0219597 A1 | 9/2007 | Kamen et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255348 A1 | 11/2007 | Holtzclaw |
| 2007/0258395 A1 | 11/2007 | Jollota et al. |
| 2008/0139910 A1 | 6/2008 | Mastrototaro et al. |
| 2008/0249470 A1 | 10/2008 | Malave et al. |
| 2008/0300572 A1 | 12/2008 | Rankers et al. |
| 2009/0058598 A1* | 3/2009 | Sanchez Sanchez ... G06F 21/32 340/5.83 |
| 2009/0077179 A1* | 3/2009 | Bi ..................... H04M 1/72547 709/206 |
| 2009/0177147 A1 | 7/2009 | Blomquist |
| 2009/0177154 A1 | 7/2009 | Blomquist |
| 2009/0227855 A1 | 9/2009 | Hill et al. |
| 2010/0010330 A1 | 1/2010 | Rankers et al. |
| 2010/0063844 A1 | 3/2010 | Reinke |
| 2010/0153832 A1* | 6/2010 | Markus ............. G06F 17/30424 715/205 |
| 2010/0198142 A1 | 8/2010 | Sloan et al. |
| 2010/0299517 A1 | 11/2010 | Jukic |
| 2010/0305421 A1 | 12/2010 | Ow-Wing |
| 2011/0033833 A1 | 2/2011 | Blomquist |
| 2011/0040247 A1 | 2/2011 | Mandro et al. |
| 2011/0047499 A1 | 2/2011 | Mandro et al. |
| 2011/0058485 A1 | 3/2011 | Sloan |
| 2011/0092907 A1 | 4/2011 | Krogh et al. |
| 2011/0119087 A1 | 5/2011 | Drucker et al. |
| 2011/0125530 A1 | 5/2011 | Drucker et al. |
| 2011/0133946 A1 | 6/2011 | Kopp |
| 2011/0151571 A1 | 6/2011 | Wooldridge |
| 2011/0166875 A1 | 7/2011 | Hayter et al. |
| 2011/0178462 A1 | 7/2011 | Moberg et al. |
| 2011/0184264 A1 | 7/2011 | Galasso et al. |
| 2011/0256024 A1 | 10/2011 | Cole et al. |
| 2011/0313784 A1* | 12/2011 | Harvey .................. G06Q 10/06 705/2 |
| 2012/0029941 A1 | 2/2012 | Malave et al. |
| 2012/0232520 A1 | 9/2012 | Sloan et al. |
| 2013/0012878 A1 | 1/2013 | Blomquist |
| 2013/0018315 A1 | 1/2013 | Blomquist |
| 2013/0331778 A1 | 12/2013 | Kruse |

OTHER PUBLICATIONS

Application No. PCT/US2012/049145, International Preliminary Report on Patentability, mailed Feb. 4, 2014, 12 pages.

* cited by examiner

THERAPY MANAGEMENT SYSTEM

CROSS-REFERENCES TO RELATED APPLICATIONS

This application claims the benefit of priority of the following U.S. Provisional Patent applications: U.S. Provisional Patent Application Ser. No. 61/513,998 entitled Therapy Management System, filed Aug. 1, 2011 by S. Daoud et al.; U.S. Provisional Patent Application Ser. No. 61/656,731 entitled Therapy Management System, filed Jun. 7, 2012 by S. Daoud et al. Priority of the filing dates of Aug. 1, 2011 and Jun. 7, 2012 are hereby claimed, and the disclosures of each of the Provisional Patent Applications is hereby incorporated by reference. This application hereby incorporates by reference in their entirety each of the following commonly-owned patents and patent applications: U.S. Provisional Patent Application Ser. No. 61/230,061 entitled Infusion System and Methods for Using Same, filed Jul. 30, 2009, by P. DiPerna et al.; U.S. patent application Ser. No. 12/846,688 entitled Infusion Pump System with Disposable Cartridge Having Pressure Venting and Pressure Feedback, filed Jul. 29, 2010 by P. DiPerna et al.; U.S. patent application Ser. No. 12/846,706 entitled Infusion Pump System with, titled Infusion Pump System with Disposable Cartridge Having Pressure Venting and Pressure Feedback, filed Jul. 29, 2010, by G. Kruse, et al.; U.S. patent application Ser. No. 12/846,720, entitled Infusion Pump System with Disposable Cartridge Having Pressure Venting and Pressure Feedback, filed Jul. 29, 2010, by D. Brown, et al.; U.S. patent application Ser. No. 12/846,733, entitled Infusion Pump System with Disposable Cartridge Having Pressure Venting and Pressure Feedback, filed Jul. 29, 2010, by M. Michaud, et al.; U.S. patent application Ser. No. 12/846,734, entitled Infusion Pump System with Disposable Cartridge Having Pressure Venting and Pressure Feedback, filed Jul. 29, 2010, by P. DiPerna, et al.; PCT Patent Application No. PCT/US2010/043789, entitled Infusion Pump System with Disposable Cartridge Having Pressure Venting and Pressure Feedback, filed Jul. 29, 2010, by P. DiPerna, et al.; U.S. patent application Ser. No. 10/200,109, entitled Infusion Pump and Method For Use, filed Jul. 19, 2002, by S. Mallett; U.S. patent application Ser. No. 11/462,962, entitled Variable Flow Reshapable Flow Restrictor Apparatus and Related Methods, filed Aug. 7, 2006, by P. DiPerna; U.S. patent application Ser. No. 12/039,693, entitled Adjustable Flow Controllers for Real-Time Modulation of Flow Rate, filed Feb. 28, 2008, by P. DiPerna; U.S. patent application Ser. No. 12/189,070, entitled Flow Prevention Regulation, and Safety Devices and Related Methods, filed Aug. 8, 2008, by P. DiPerna; U.S. patent application Ser. No. 12/189,064, entitled System of Stepped Flow Rate Regulation Using Compressible Members, filed Aug. 8, 2008, by Paul DiPerna; U.S. patent application Ser. No. 12/538,018, entitled Two Chamber Pumps and Related Methods, filed Aug. 7, 2009, by Paul DiPerna; U.S. patent application Ser. No. 12/020,498, entitled Two Chamber Pumps and Related Methods, filed Jan. 25, 2008, by Paul DiPerna; U.S. patent application Ser. No. 12/468,795, entitled Disposable Pump Reservoir and Related Methods, filed May 19, 2009, by Paul DiPerna; U.S. patent application Ser. No. 12/260,804, entitled Flow Regulating Stopcocks and Related Methods, filed Oct. 29, 2008, by Paul DiPerna; U.S. patent application Ser. No. 12/393,973, entitled Slideable Flow Metering Devices and Related Methods, filed Feb. 26, 2009, by Paul DiPerna; U.S. patent application Ser. No. 12/714,299, entitled Methods and Devices for Determination of Flow Reservoir Volume, filed Feb. 26, 2010, by Michael Rosinko et al.; U.S. patent application Ser. No. 12/563,046, entitled Solute Concentration Measurement Device and Related Methods, filed Sep. 18, 2009, by David Brown; U.S. patent application Ser. No. 61/392,858, entitled Analyte Monitoring Systems and Methods of Use, filed Oct. 13, 2010, by David Brown et al.; PCT Patent Ser. No. PCT/US2009/044569, entitled Disposable Pump Reservoir and Related Methods filed May 19, 2009, by Paul DiPerna; U.S. patent application Ser. No. 61/054,420, filed May 19, 2008, by Paul DiPerna; PCT Patent Application Ser. No. PCT/US2009/057208, entitled Flow Regulating Stopcocks and Related Methods, filed Sep. 16, 2009, by Paul DiPerna et al.; U.S. patent application Ser. No. 61/054,420, entitled Disposable Pump Reservoir and Related Methods, filed May 19, 2008, by Paul DiPerna; U.S. patent application Ser. No. 61/097,492, entitled Flow Regulating Stopcocks and Related Methods, filed Sep. 16, 2008, by Paul DiPerna; U.S. patent application Ser. No. 61/156,405, entitled Methods for Determination of Pump Sensor Integrity and Calibration of Pumps, filed Feb. 27, 2009, by Michael Rosinko et al.; U.S. patent application Ser. No. 61/184,282, entitled Methods and Devices for Determination of Flow Reservoir Volume, filed Jun. 4, 2009, by Michael Rosinko et al.; PCT Application No. PCT/US2009/057591, entitled Solute Concentration Measurement Device and Related Methods, filed Sep. 18, 2009, by David Brown; U.S. patent application Ser. No. 61/098,655, entitled Solute Concentration Measurement Device and Related Methods, filed Sep. 19, 2008, by David Brown; U.S. patent application Ser. No. 61/102,776, entitled Solute Concentration Measurement Device and Related Methods, filed Oct. 3, 2008, by David Brown; U.S. Pat. No. 7,008,403, entitled "Infusion Pump and Method for Use" by S. Mallett; U.S. Pat. No. 7,341,581, entitled "Infusion Pump and Method for Use" by S. Mallet; U.S. Pat. No. 7,374,556, entitled "Infusion Pump and Method for Use", by S. Mallet; U.S. Patent Application Publication No. 2007/0264130, entitled "Infusion Pumps and Method for Use", filed May 4, 2007 by S. Mallett; and U.S. Patent Application Publication No. 2009/0191067, entitled "Two Chamber Pumps and Related Methods", filed Jan. 25, 2008 by P. DiPerna; U.S. Provisional Patent Application Ser. No. 61/511,220 filed Jul. 25, 2011 by P. DiPerna et al. and entitled "Multi-Reservoir Infusion Pump Systems and Methods, and U.S. patent application Ser. No. 13/474,032, entitled "Methods and Devices for Multiple Fluid Transfer", filed May 17, 2012 by T. Metzmaker et al. All of the above-listed patents and applications are incorporated by reference herein in their entirety.

BACKGROUND

Many electronic devices maintain a data log of information to keep a record of their operational status, use history, and other parameters. Such electronic devices can be used for controlling a variety of operations, such as transmitting data. In the context of electronic medical devices such as infusion pumps and the like, they may be used for dispensing or releasing medicaments, including fluids and other materials such as insulin and related medicaments. The data log may provide, for example, a history of transmitted or received data, data associated with substances or fluids such as on-board and dispensed volume, composition, lot number, and other characteristics, as well as operational parameters relating to transmitting, dispensing or releasing such substances or fluids. These electronic devices may not include sufficient memory to maintain a running, cumulative record of these data over an extended time period, or there may be a need for such cumulative data or other non-cumulative data to be backed-up, mirrored, or simply stored elsewhere for archival or other purposes. Therefore, these data may be maintained at one or more locations that are remote from the device, such as, e.g., a remote computing device or a network data storage facility that may have more extensive data storage capacity than that on the electronic device. As the device continues to operate, data such as those comprising a data log and/or other operational information (which such operational information may or may not be in a data log) may need to be sent to, transferred to, or otherwise maintained at a remote location such as a network data storage site to meet various needs of the users of and manufacturers of such devices.

In most cases, privacy concerns for the data generated by the electronic device will encourage careful control of access to such data by using a variety of authorization schemes. If the device is used for medical or patient care purposes, then such privacy and other data security concerns may mandate data security schemes. In the U.S., for example, the Health Insurance Portability and Accountability Act (HIPAA) of 1996 established national standards for electronic health care transactions and for the security and privacy of health data. Other such privacy mandates for patient-related and consumer-related data exist outside the U.S. as well.

For example, portable medicament infusion devices, such as infusion pumps, are used to regulate the dispensing of fluids such as insulin and other medicaments to a patient. These electronic devices may be in constant or frequent operation and may store data relating to, e.g., the dispensing of medicaments such as insulin to the patient, data relating to various operational parameters of the pump, and the like. Such data, particularly if it is cumulative in nature, may be more than can be accurately and safely stored in the memory of the infusion device itself. It may also be desired to store all or selected portions of such data at one or more alternative sites such as, e.g., a remote computing device or a network data storage facility. Such remote locations may be used to archive such data, enable analysis thereof for the patient, the health care provider, the manufacturer, and even government regulatory authorities, and for other purposes. It is therefore desirable to maintain some or all of such data in a format that is available to meet such needs.

It is known to establish and use network data facilities for storage of data such as portable insulin pump data. Access to such data, however, can be cumbersome and protracted. In some cases, access to the network stored data requires the presence of the actual insulin pump at the computer or other device being used to obtain access. In other cases, data transfer can be a relatively slow and cumbersome process. Moreover, once access to such data is granted and an authorized communication path is established, it may be desirable or necessary to carefully control such access so that third parties are not able to use the communication path to gain unauthorized access to the data.

Easier access to the network stored data and more secure data transfer are desired improvements. The present invention addresses these needs.

SUMMARY

Disclosed herein are techniques for accessing stored data over a computer network through a network data manager. In one aspect, a request message containing an access requestor identifier is received at the network data manager from a client device for access to a data storage facility. The network data manager determines if the access requestor identifier is associated with a data record that identifies a product device having a registration record, and if it does, the network data manager transmits a data link to the client device, wherein the data link provides access to the data record by the client device over the computer network for a predetermined time period such that access to the data record is halted upon expiration of the predetermined time period. The client device may comprise, for example, a desktop or laptop computer. The product device, for example, may comprise a portable insulin pump that can be connected to the computer for data transfer to and from the network data manager.

In another aspect, data transfer over a computer network from a product device is accomplished with an uploader application executing at a host device, such that the uploader application authenticates the product device, extracts a data log from the authenticated product device, and uploads the extracted data log to a data record at a data storage facility over the computer network. The uploader application can receive a data link at the host device from the network data manager in response to uploading of the extracted data log, and generates a display of the received data link, wherein the data link provides access to the data record by the host device over the computer network for a predetermined time period such that access to the data record is halted upon expiration of the predetermined time period.

In other aspects, access to data is controlled such that access is automatically terminated such that an unattended but previously authorized device cannot be used to gain access. For example, the network data manager may send an access grant message to the client device for access to the stored data and receives a data request back from the client device. The network data manager will then provide the requested data record to the client device over the computer network only if the predetermined time period for the data link has not expired. In this way, access to the stored data is securely controlled and unauthorized access is less likely. In yet another aspect, the product identifier associated with the registration record at the network data manager may relate to a product device, and the product device and client device may be integrated together into a single device. For example, the product device (and client device) may comprise an insulin pump device that directly communicates with the network data manager.

Other features and advantages of the present invention should be apparent from the following description of preferred embodiments that illustrate, by way of example, the principles of the invention.

DETAILED DESCRIPTION

Figure 1:
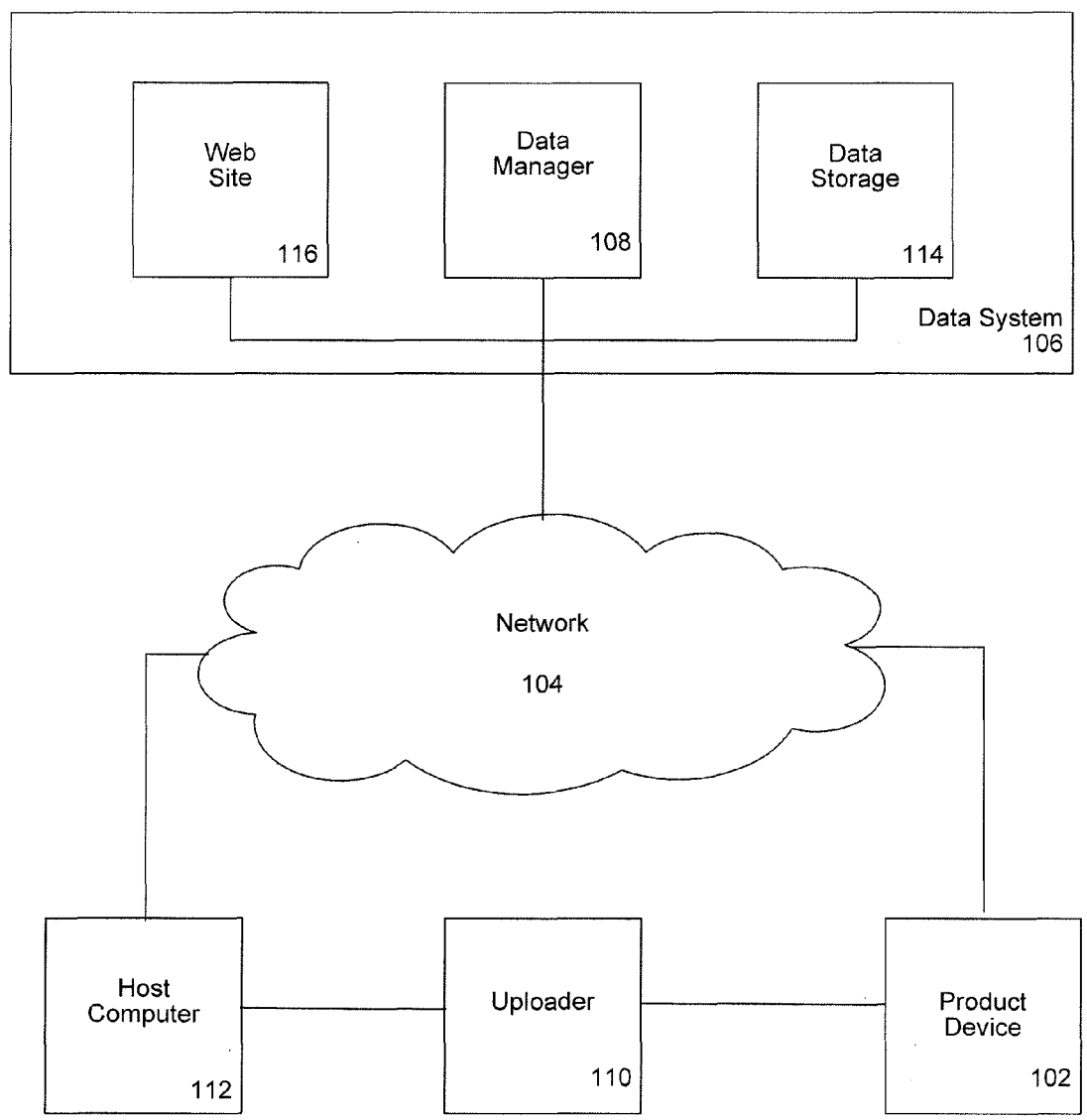
FIG. 1 is a block diagram of a system in accordance with the invention.

FIG. 1 is a block diagram of a system in accordance with the invention that shows a product device 102 that communicates over a computer network 104 with a data system 106. The product device communicates with a network data manager 108 through an uploader application 110. The uploader is a computer software application that performs operations of authentication and data transfer between the product device 102 and the network data manager 108. The uploader typically is installed at a host computer 112. The uploader application 110 manages, e.g., product device authentication, transfer of product device data from the product device to the network data manager, and receipt of stored product device data from the data manager. That is, the uploader application is a network client of the network data manager. Product device data may include, for example, operational details of the device, information regarding a history of transmitted or received data, data associated with substances or fluids such as on-board and dispensed volume, composition, lot number, and other characteristics, as well as operational parameters relating to transmitting, dispensing or releasing such substances or fluids.

The uploader application 110 of the system of FIG. 1 communicates with the data manager 108 while executing on a device having a processor, memory, display, and network communication interfaces sufficient for communication with the network data manager. Other computer resources for more convenient operation may be provided as well. Typically, the uploader application is hosted on the host computer 112 and the host computer is a client device to the network data manager. The host computer communicates with the product device 102 for product data including data logs, which the host computer transfers to the network data manager 108. Thus, the host computer 112 and product device 102 and uploader application 110 comprise a system for transferring data over the computer network 104. If the product device 102 has sufficient resources, such as a processor, memory, display, and network communication interfaces, then the uploader application 110 can reside on, e.g., the product device, and in that situation the product device can communicate directly with the network data manager 108 over the network 104. Additionally in that case, the host computer 112 and the product device 102 are integrated together into a single device that hosts the uploader application 110 and is a client device to the network data manager. That is, the integrated host computer and product device comprise a system having sufficient resources, such as a processor, memory, input/output components, and network communication interfaces, to carry out the functions described herein.

The network data manager 108 of the data system 106 may receive a request message for access to data stored at a data storage facility 114. The data storage facility is adapted to store large amounts of data for access by computers and may comprise, for example, multiple disk drives, solid state disk drives, semiconductor memory, and/or other suitable storage devices. The data stored at the data storage facility 114 may comprise all or portions of data transferred from the product device 102, including the product device data noted above. The request message includes an access requestor identifier, to identify an owner of a product device or to identify a third party who is neither the owner of the product device nor the network data manager. The third party may comprise, for example, a physician and/or an authorized member of the physician's staff, a representative from a partner device producer, a clinician, a certified diabetes educator (CDE), and the like. If the network data manager determines that the access requestor identifier is associated with a data record that identifies a product device that has a registration record or that otherwise identifies an authorized party, such association may be used to confirm that the access requestor has been authorized. The data record to identify authorized parties may be generated through a process such as a prior registration process with the data storage facility 114 through the network data manager 108. That is, a registration record for a product device 102 includes identifiers of any product device owners or third parties who have registered with the network data manager or have otherwise been previously authorized to gain access to data of the product device.

As explained in greater detail below, third parties may register with the network data manager in response to an invitation initiated by a product device owner and sent to the third party. In the exemplary embodiment described herein, the network data manager generates an invitation request pop-up window to a user who has logged in to their account and who requests inviting someone with whom the user will share data. The third party responds to the invitation by providing registration information to the network data manager, which stores the registration information in a data record that is associated with the product device 102. The registration data record is stored in the data storage 114 along with other information relating to the product device, such as product model number, serial number, name and address of purchaser (owner and/or user) of the product device, and the like. Additional data that may be maintained in the registration data record will depend on the product device. For example, if the product device is a portable insulin pump, additional data in the registration data record may relate to therapy settings for the pump, such as insulin delivery settings, daytime settings, night settings, dosage size and frequency, and the like, as described, for example, in U.S. patent application Ser. No. 12/846,688 to DiPerna et al. filed Jul. 29, 2010. Other data that may be acquired and stored in the registration record includes the email address used as the user name to login to the network data manager, the password used to authenticate the user, a secret question (e.g. selected by the registrant from a list) and the answer to the secret question, date of birth. If the user is under 13, in addition to capturing the patient's information mentioned above, the system also maintains registration information from the caregiver or the parent, such as first name, last name, email address, and date of birth for the caregiver or parent. Some or all of the information described above may be maintained in the registration information, depending on whether the registrant is a user of the product (patient) or a third party.

After the network data manager 108 determines that the access requestor is authorized, the network data manager transmits a data link to the requesting client device, wherein the data link provides access to the data record by the client device over the computer network 104 but automatically expires, canceling access. For example, the data link may be active only for a predetermined time period, such that access to the data record is halted upon expiration of the predetermined time period. The data link typically comprises an Internet link that is accessed via an Internet browser application executing on the client device. Accessing the Internet link takes the browser application to a Web site 116 in accordance with the authorization of the data manager 108.

Figure 16:
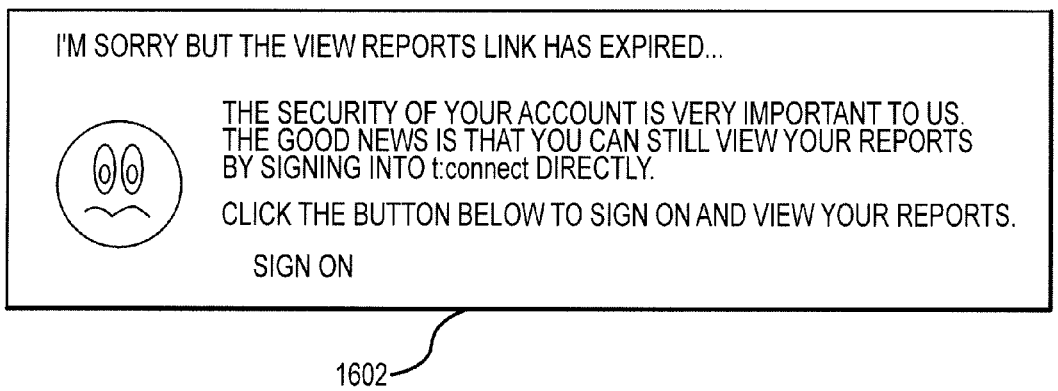
FIG. 16 is a screen shot for a computer accessing the network data manager that shows automatic cancellation of the data link.
Figure 17:
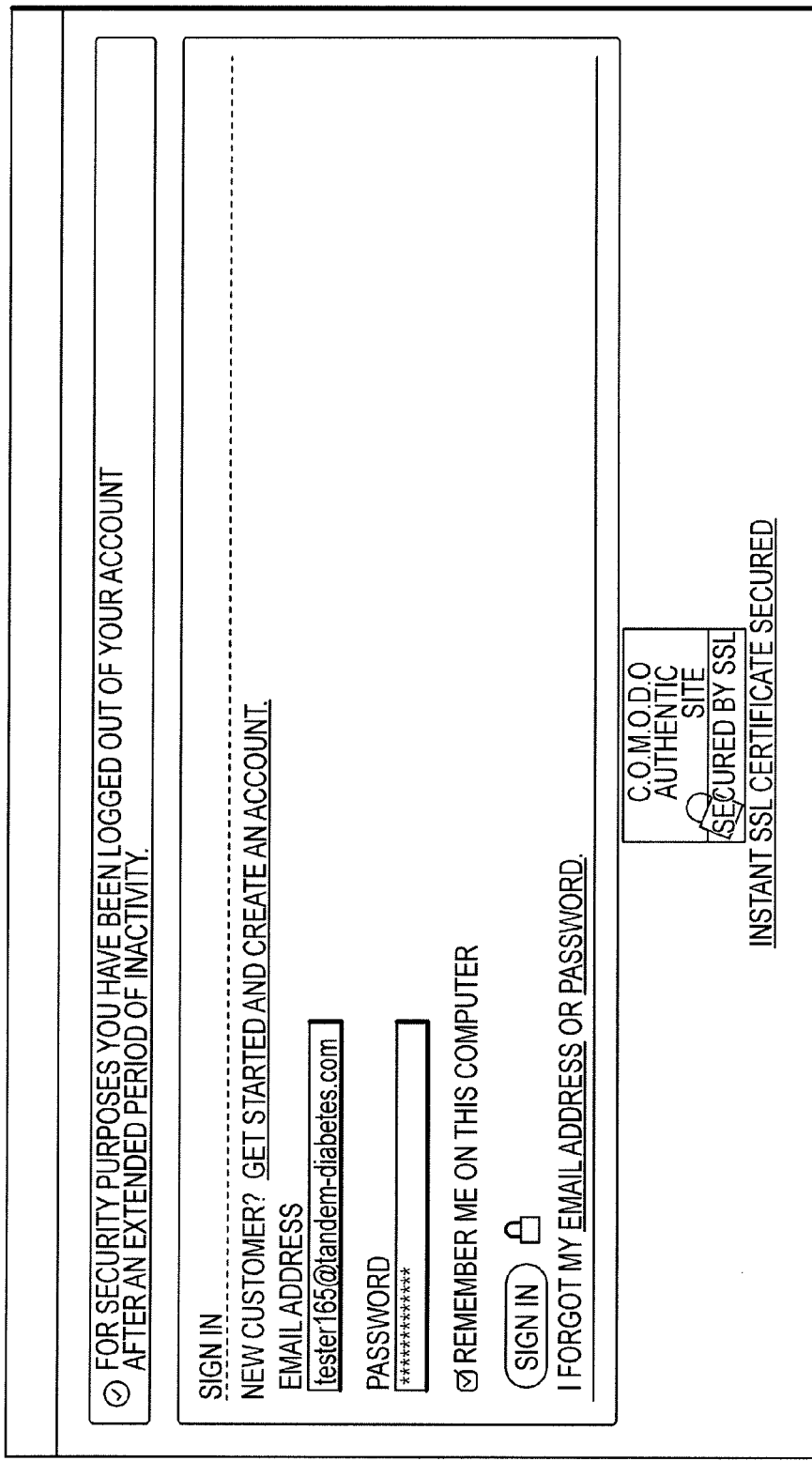
FIG. 17 is a screen shot for a computer accessing the network data manager that shows automatic logout of an inactive user.

Attempting to access the data link after it has been canceled will result in an expired link message. This increases data security and helps safeguard the privacy of user data. For example, FIG. 16 shows a pop-up window 1602 that appears in a browser if a user is accessing the network data manager through an Internet browser application and has attempted to access the data link after it has been canceled. Other means of providing automatic canceling of the data link may be provided, such as requiring a supplemental authentication step to remain active, where the supplemental authentication step may require entering a password, providing biometric input, or the like. The automatic canceling of the data link helps limit the chance of unauthorized access or viewing, such as where a legitimate user gains access through a desktop computer and then leaves the computer unattended. When the link is canceled, the report window is closed. The automatic canceling of the data link ensures that a stranger who comes upon the computer after the link has been canceled will not be able to view data or otherwise gain access to the data storage facility 114. If automatic canceling is provided by a time-out period, then the expiration time can be set to a default time period that best maintains confidentiality while being convenient for a legitimate user, or may be configured by a user upon authorized registration. It should be noted that the canceled link is a safeguard in addition to automatic logout of a user, which may occur after an extended time period of inactivity. FIG. 17 shows a logout window 1702 such as would be displayed after a user has been inactive, after first logging into the network data manager facility. The logout action of FIG. 17 helps to make more efficient use of system resources, so that users who are idle can be logged out to make room for other users who are attempting to gain access to the network data manager.

Figure 2:
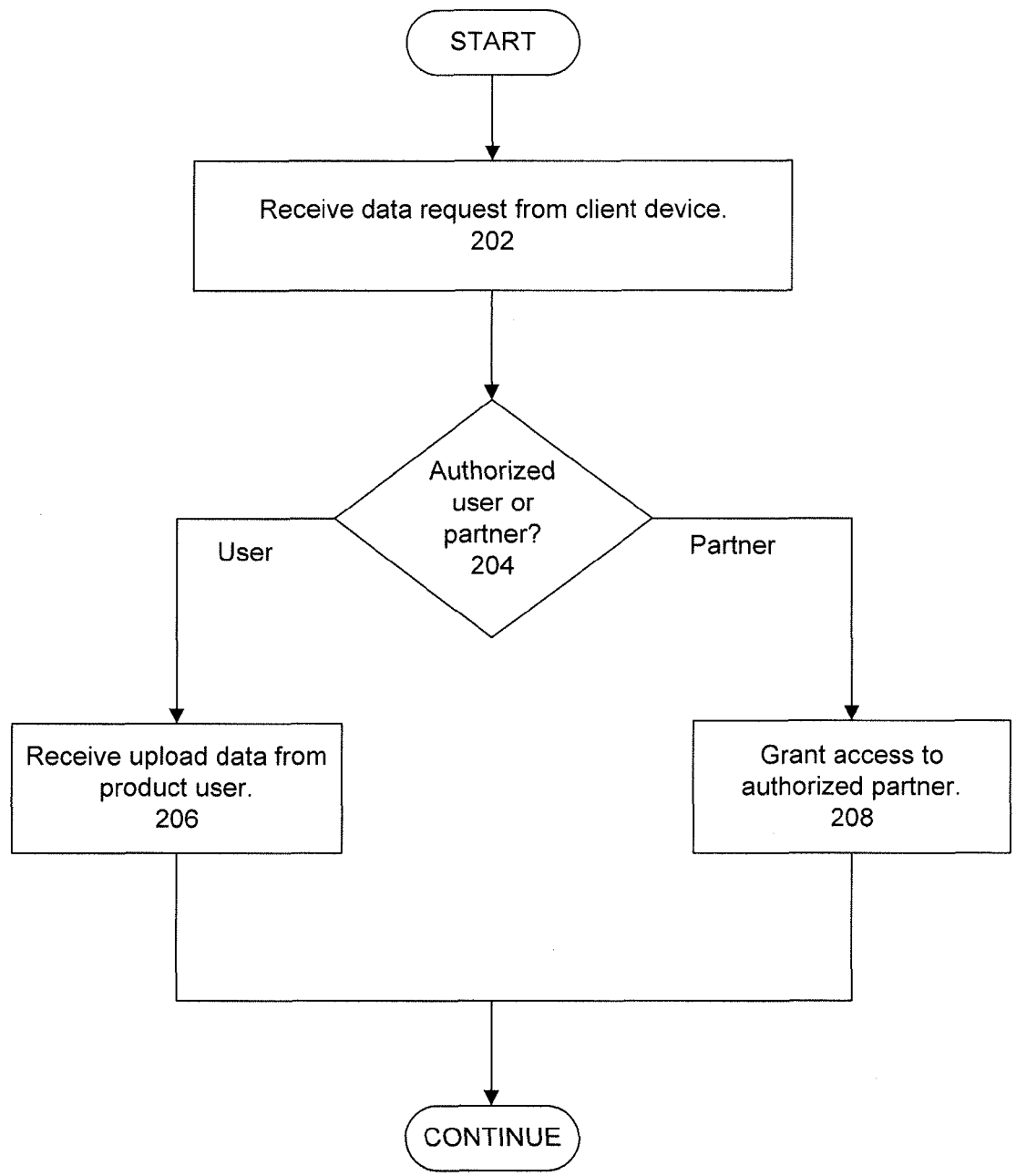
FIG. 2 is a flow diagram that illustrates operation of the data manager of FIG. 1 in authenticating.

FIG. 2 illustrates the operation of the network data manager 108 illustrated in FIG. 1. The illustrated operation begins at the flow diagram box numbered 202, where the network data manager receives a data request from a client device. As noted above, the data request includes an access requestor identifier. Next, at the decision box numbered 204, the network data manager determines if the data request comes from a registered user (such as an owner of a product device who is associated with a registration record for the product device) or if the data request comes from an authorized partner (such as, in the context of a medical device such as an infusion pump or the like, a physician, physician's authorized representative, personnel at an authorized medical clinic, etc., who has replied to an access invitation message associated with the product device and who has registered with the network data manager). If either of these conditions is true, then access can be granted. Thus, if the data request is from an authorized user, then at box 206 the network data manager can receive upload data from the client device, and normal operation then continues. The received upload data may comprise any data capable of being transferred from the device, including the product device data described above. If the data request is from an authorized partner, then the network data manager will grant access in response to the data request and normal operation then continues. If neither authorized situation applies, then the data manager will not grant access in response to the data request.

The data request from an authorized user may be automatically initiated by the device upon becoming activated or achieving network access. For example, when the device gains network data access, it may automatically send a message to the network data manager that requests access or login to the account associated with the device. The message may take the form of an email message or a mobile telephone text message or message forwarded from a social network facility, or the like. The data request from an authorized partner may comprise a message to the network data manager that initiates a login process by the authorized partner to log in to their own account. Again, the message may take the form of an email message or a mobile telephone text message or social network message or the like. The authorized partner typically must accept an invitation from an authorized user to establish an account and share the user's data. Once an authorized partner has established an account with the network data manager, the authorized partner can view a list of patients from whom they have received data sharing invitations and may choose a patient's name from the list, upon which they are granted access to view the data. The data request will typically be received through the Web site 116 (FIG. 1), which can initiate error processing or otherwise provide the data requestor with options to provide additional information to become registered and gain access, where appropriate. Whatever form the data request message takes, be it email, text, or message through social networks, the message will be addressed to the network data manager and, once received, will be acted upon.

Figure 3:
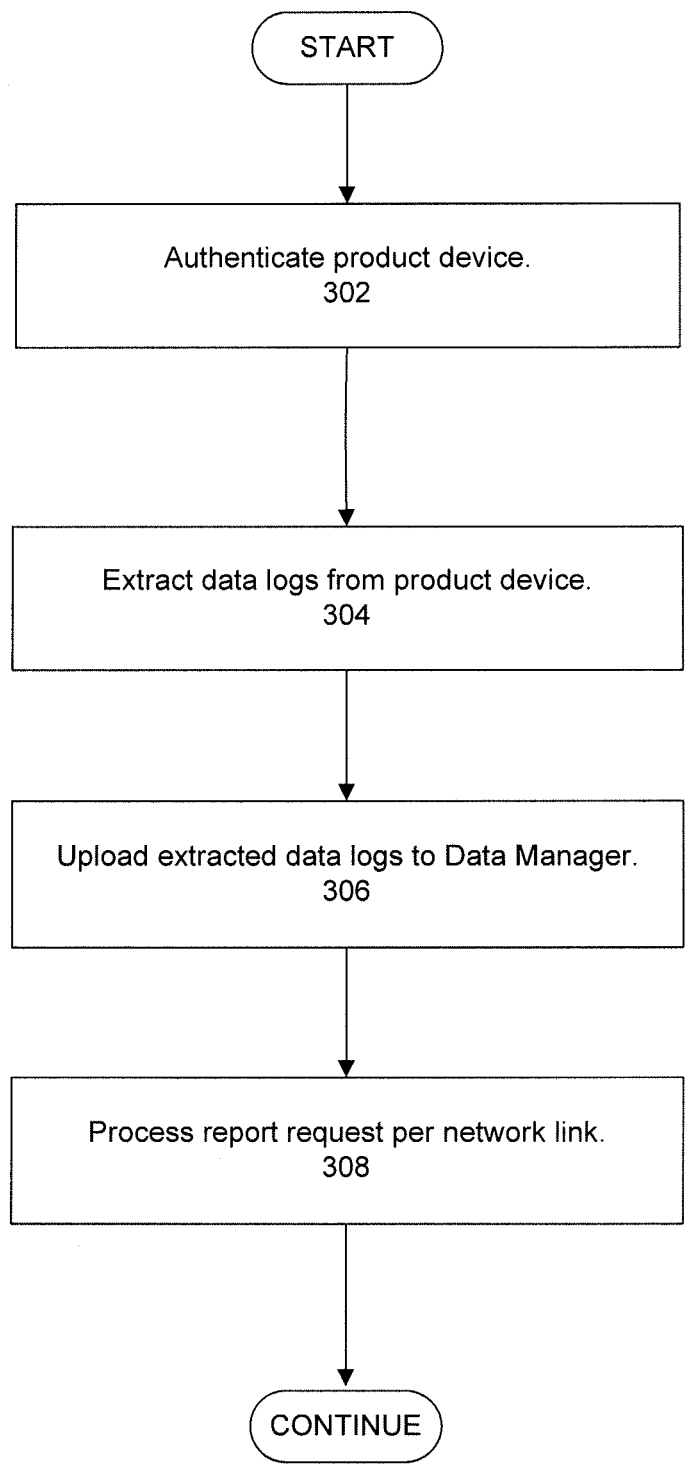
FIG. 3 is a flow diagram that illustrates operation of the uploader of FIG. 1 in processing a product device.

FIG. 3 illustrates the operation of the uploader application 110 illustrated in FIG. 1. The uploader application is installed in a host device, such as a desktop or laptop computer, mobile computing device such as a mobile phone, tablet computer or the like, or the uploader application 110 may be installed in the product device itself. In either case, the first operation illustrated in FIG. 3 is represented by the flow diagram box numbered 302, which shows the uploader operation to authenticate the product device. The operation to authenticate the product device is initiated by launching the uploader application, which may be manually launched by a user of the uploader application, or may be automatically launched. Automatic launch of the uploader application may occur in response to connecting the product device to the host device, in the case of a separate product device and a host device that executes the uploader application, or automatic launch may occur in response to a suitable network connection that becomes available to the uploader application. Automatic launch in response to a suitable network connection may comprise, for example, a network interface of the host device or product device that detects a broadband connection such that relatively high speed data communications with the network data manager will be supported. For example, upon coming within range of a broadband "WiFi" network, the device may attempt to establish a communication session with the network and, upon logging on, the uploader application 110 may be launched. The automatic uploader launch may be in place of, or in addition to, the automatic data request message described above.

Once network communication is established by the uploader application, the uploader sends a data request message to the network data manager, providing an access requestor identifier. The access requestor identifier may comprise, for example, the product device serial number and/or product number or other indicator of the device's authenticity, registration, and ownership data, an email address and/or password combination, user name and/or password combination, or other login identifier information by which registered users may be identified, including combinations thereof. Any combination of one or more of such information may be used as the access requestor identifier to uniquely identify a person who is requesting access to the data of the device that has been transferred to the network data manager. If the network data manager determines that the access requestor identifier is associated with a data record that identifies a product device having a registration record, the data requestor is authenticated. That is, the network data manager identifies product user registration data that is associated with the login information and that is associated with the product device. The network data manager then sends an access grant message to the client device to confirm that access to the stored data has been granted.

At the uploader application, data logs are extracted from the product device, as indicated by the flow diagram box numbered 304. The product device stores a log of operational information and records an index of upload events to keep track of the last uploaded data log with changed data. For example, in the case of a product device that is a portable medicament infusion device such as a portable insulin pump, after an upload occurs, an index number is increased by one incremental value when a change is made to the data log. The uploader application will not transfer data logs if the index number is not greater than the index number of the last upload event. In this way, duplicate data log records will not be extracted and will not be transferred to the network data manager.

For example, continuing with the case of a portable medicament infusion device such as a portable insulin pump, if an insulin dosage is delivered to the patient, the pump recognizes that the delivery is a change in its operational history, and records that event in the data log as a change. The time and dosage amount is recorded in the data log and the data log index number is incremented. If another change occurs, such as a dose delivery, or a change to device parameters such as dosage times or the like, then the data log index number is again incremented. The device discriminates between events that should initiate a log index increment and those events that should not. For example, uploading data from the device, and applying electrical power to the device, are examples of detected events that initiate a log index increment by the device. Entering values on the device keypad but not entering or submitting the values that would otherwise proceed with processing is an example of an event that would not initiate a log index increment. The device is adapted to increment the log index in response to events that have been determined to be worthy of recording at the network data manager. Upon a requested upload, the current index number will be different from the index number at the time of the last successful upload, and therefore an upload event will occur. That is, after device authentication, the network data manager sends the last index number that the network data manager received in an upload, so that the uploader application only extracts data based on the index number it received from the network data manager. As a result, the data log beginning from after the previously uploaded data log at the old index number, through the data log at the current index number, will be transferred to the network data manager. If the current index number is the same as the index number of the last upload, then the uploader application recognizes that no data change has occurred since the last upload, and the uploader application will not perform an upload.

In this way, the network data manager keeps track of the index numbers on the device and sends the index number of the last uploaded data to the device so that the uploader application extracts data from the data log for sending to the network data manager based on the difference between in index number received from the network data manager and the current index number in the data log of the device.

After the changed portion of the data log is identified, the changed data is extracted for transfer to the network data manager. This operation is represented by box 306 in FIG. 3. The extracted data log and corresponding change items are then transferred to the network data manager. After a successful upload is received at the network data manager, the network data manager provides a confirmation that produces a window display at the client device (i.e. host device or product device) that permits the user to request access to a data record for viewing of a report, or printing of a report, or both. The window display typically comprises a data link that is sent from the network data manager to the client device, such that the data link can be viewed with an Internet browser application. Viewing the data link provides access to the data record by the client device over the computer network until the data link is automatically canceled, as noted above. That is, the browser is unable to view the data record through the data link after the data link has been canceled, such as after a predetermined time period has expired. This provides data security so that only authorized users may gain access to the data records associated with a product device. If the data link is canceled after a predetermined time period, then the predetermined time period may be set in accordance with privacy or other security needs. A time period of ten minutes should suffice under most circumstances, to provide a user with time to access and view or print the reports.

At box 308 of the uploader application processing, the network data manager receives any requested data record viewing or printing request from the client device via the data link, and processes the request to deliver the requested information, either a window view or a print file. Normal operation then continues.

Operation of the uploader application will be better understood with reference to the state diagrams of FIGS. 4-10 that illustrate operations of the uploader application.

Figure 4:
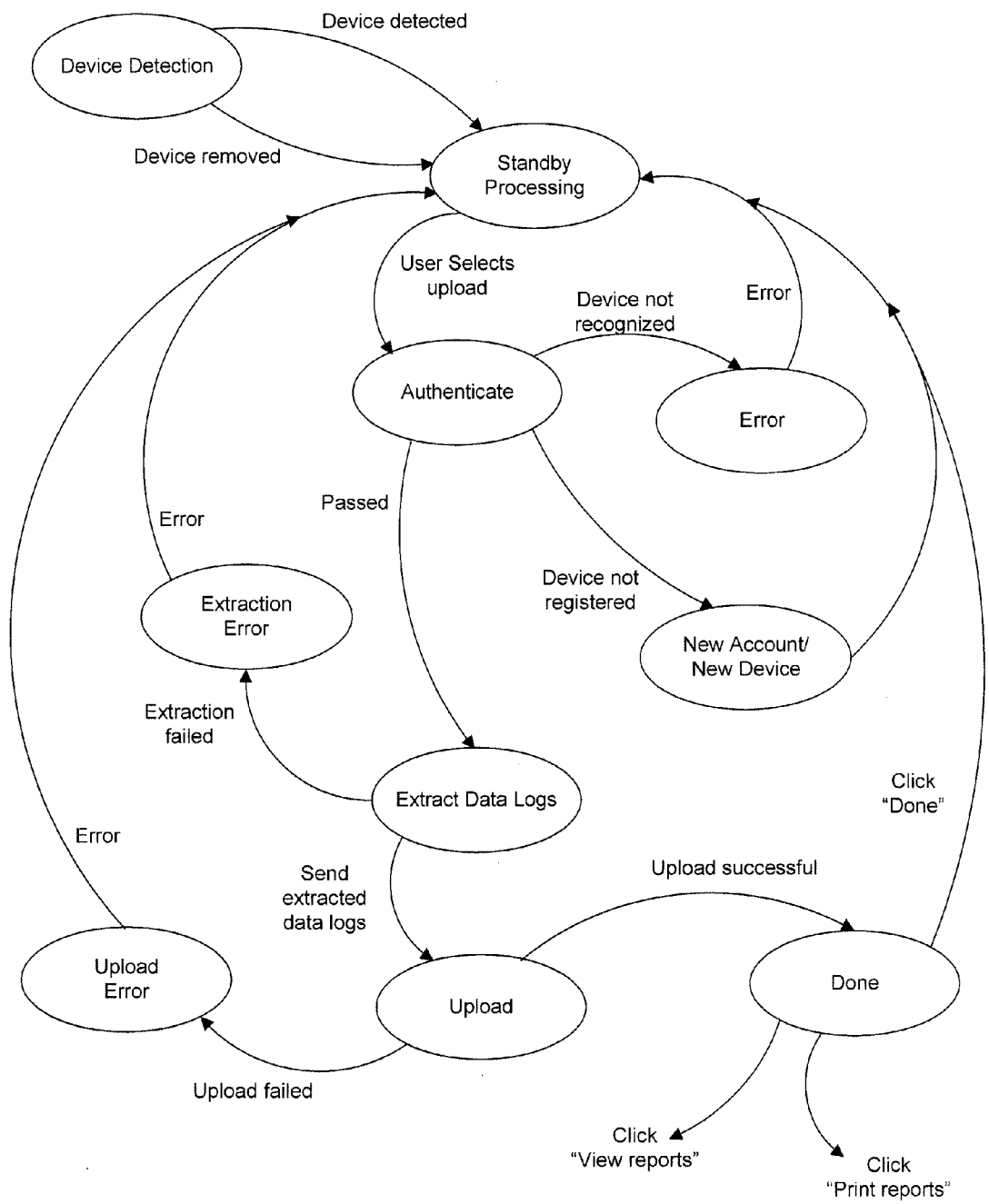
FIG. 4 is a state diagram that illustrates operation of the uploader of FIG. 1.

FIG. 4 shows that operation of the uploader application begins in the Device Detection state and remains there until a device detected or device removed event. The device detected event occurs when a product device 102 is connected to the host computer 112 or the product device 102, or otherwise gains access to the network 104 (see FIG. 1). For example, the uploader application may remain in the Device Detection state until the product device integrated with the uploader application gains network communication, or until the product device is connected to a host device, which may or may not have an existing network communication. A device removed event occurs when the product device 102 is disconnected from the host computer 112 or the product device otherwise loses access to the network 104.

Upon occurrence of a device detected event or device removed event, the state of the uploader application changes to the Standby Processing state, in which the uploader application remains until the user initiates an "upload" operation. If the device includes an optional GUI (graphical user interface) display that is produced by the uploader application for product devices containing GUI displays, then the user may select an upload operation from the GUI display window. For devices with a GUI display, the upload operation selection may be accomplished via a linked icon or button of the GUI display. The GUI display with selectable upload operation may be produced on a display of the host device or on a display of the product device, or both.

After the user selects the upload operation, the state of the uploader application changes to Authenticate, at which time the uploader application initiates authentication processing. The authentication processing may result in one of three outcomes: (1) the product device is not registered with the network data manager, (2) the product device is not a recognized device that is maintained in the network data manager database, or (3) the product device is recognized and is registered (a "passed" outcome).

The processing to determine the authentication outcome involves determining if the product device is associated with a registration record that identifies a registered user of the product device, in which case the authentication passes, and otherwise indicating that a registration process must be completed for the product device in response to determining that the product device is not associated with a registration record that identifies a registered user of the product device, or indicating that the product device is not recognized as a valid device for the uploader application.

If the product device is not recognized, then the state of the uploader application changes from the Authenticate state to the Error state, and uploader application processing subsequently returns to the Standby Processing state with an appropriate error message (e.g. "Product not recognized") that is generated in the Error state. If the product device is recognized but no registration record can be identified, then the state of the uploader application changes from the Authenticate state to the New Account/New Device state, in which the uploader application provides an appropriate message such as a request to the user to register the product device. The user may be required to establish a user account after verifying data relating to user patient status, payment, and the like. The uploader application processing subsequently returns to the Standby Processing state, once registration is complete. The user may then request the upload operation.

If the user is authenticated, then the state of the uploader application changes from Authenticate to Extract Data Logs. If the data logs are successfully extracted as described above in connection with FIG. 3, then the uploader application sends the extracted data logs to the network data manager and the state of the uploader application changes to Upload. If the extraction of data logs fails, such as if communication with the product device is lost, then the state of the uploader application changes from Extract Data Logs to Extraction Error, in which case an appropriate data message error message (e.g. "Extraction Error") is generated and the state of the uploader application changes to the Standby Processing state to await the next user operation.

If authentication is successful, and if extraction of data logs is successful, then the state of the uploader application is in the Upload state, where the outcome of the state is either a successful upload or a failed upload. If the upload is successful, then the state of the uploader application changes to Done, and the user is presented with a display that offers choices between obtaining reports and completing operations. For example, FIG. 3 shows three choices comprising (1) view reports, (2) print reports, or (3) selecting Done. Selecting "view reports" permits the user to view a report online through the display of the device or through a Web browser, selecting "print reports" permits the user to print a report at a connected printer, and selecting "done" results in the state of the uploader application changing to the Standby Processing state, to await the next user operation. The display of post-upload selectable operations may be produced on a display of the host device or on a display of the product device, or both. If the upload operation failed, then the state of the uploader application changes to indicate an upload error, an error message is displayed, and the state of the uploader application changes to the Standy Processing state.

As noted above, a successful device authentication and a successful data log extraction (upload) results in a state of "successful upload" and the user is presented with a "successful upload" display that offers choices between obtaining reports and completing operations. For increased security, an embodiment of the system guards against a "spoofed" device or other attempt at establishing communication by an unauthorized person with an unauthorized device. For example, the "device" may actually be a computer being used to mimic a device, for the purpose of surreptitious or nefarious data access. To guard against such possibilities, the operation in FIG. 4 of the "Upload" state with output of "Upload successful" may be configured so that the device is confirmed before the "successful upload" display is provided to the device.

Confirming the device may comprise sending a request for confirmation information to the device and then validating the received response. For example, the network data manager may request the device to provide a randomly selected data record from a randomly selected time in the history of the device operation. When the confirmation response is received from the device, the network data manager can check the response to ensure that it contains correct information. The network data manager can check for correctness because the network data manager has a record of the device history, via prior data uploads from the device, and therefore the data records received from the device in response to the confirmation request should be identical to the corresponding data record previously received at the data manager from the device for the selected data record and selected time. If they are identical, then the response to the confirmation request is validated.

For example, the data manager might request that the device provide its bolus setting at 12:30 pm on Aug. 1, 2012. The data manager will have previously received exactly that data via a previous upload from the device. If the device seeking to establish communication is a legitimate device and is the same device from which the prior upload was received, then the device seeking to establish communication should be able to provide the requested information. If the device does not provide the correct information, the data manager will conclude that the device is an imposter and will not confirm the device, and therefore the user of the device will not be presented with a "successful upload" display and will not be offered a choice between obtaining reports and completing operations.

Over time, the uploaded data received at the network data manager from the device will comprise a relatively large body of data from which the network data manager may choose for confirmation requests. The network data manager is free to request confirmation data from the device according to any and all data available to the network data manager and to a legitimate device. The body of data from which the network data manager may select can comprise all the operating history data stored at the device, which will be determined by the storage capacity of the device itself. The initial communication with the device may take place upon manufacturing, with an initial set of upload data from which the network data manager can select for confirming requests. The network data manager can then select from the body of data with which the device has been initiated. Alternatively, the initial communication may not include storing an initial set of data into the device. In that scenario, the initial confirmation request from the network data manager may involve administrative information known only to a legitimate device, such as device serial number, production date and time, power-on date and time, and the like.

If the device is confirmed, then the selectable post-upload options are provided in a window display at the client device (i.e. host device or product device). As described above in conjunction with FIG. 3, the window display typically comprises a data link that is sent from the network data manager to the client device, such that the data link can be viewed with an Internet browser application. Viewing the data link provides access to the data record by the client device over the computer network for a predetermined time period, such that access to the data record is halted upon expiration of the predetermined time period.

Figure 5:
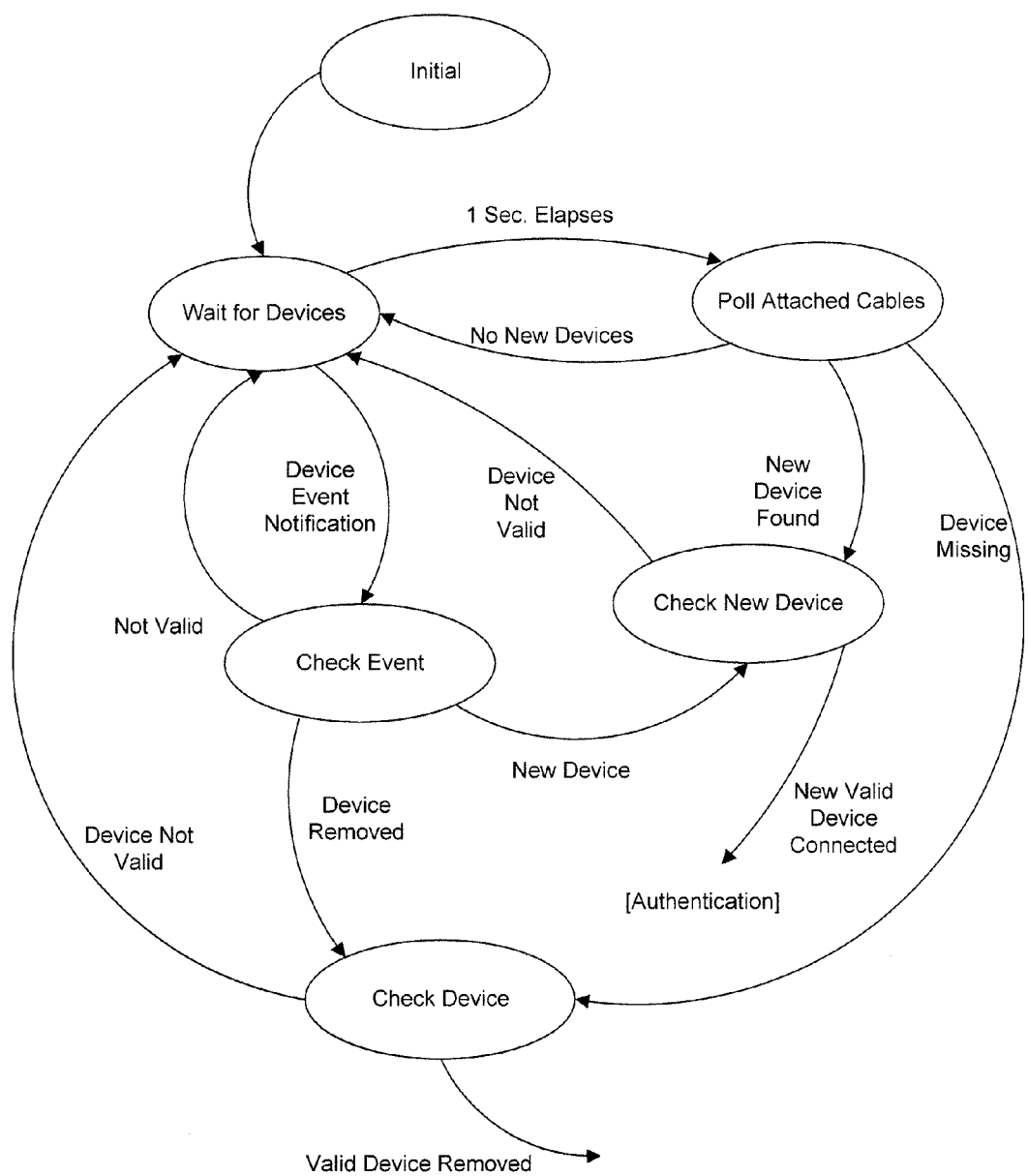
FIG. 5 is a state diagram that illustrates the device detection operation shown in FIG. 4.

FIG. 5 illustrates the operation of the uploader application in the Device Detection state shown in FIG. 4. In the Device Detection state, the uploader application begins in an Initial state, waiting for notifications regarding device registration. After a brief wait in the Initial state, involving any system activities for launch of the uploader application, the uploader application changes state to the Wait for Devices state. A default configuration for the uploader application to communicate with product devices is to communicate with such devices via a cable connection. Therefore, the uploader application remains in the Wait for Devices state until it receives a notification of a "device connected" event, at which time the state changes to Check Event, or the uploader application automatically changes to a Poll Attached Cables state after a one second time interval of waiting. An alternative to a cable (electronic, optical or otherwise) connection is for the product device to be connected to the host device via wireless connection, such as by infrared (IR) transmission, or by radio frequency (RF) transmission. The RF connection may be through, for example, particular protocols such as "Bluetooth" or "WiFi" or the like. Similarly, the connection from the product device to the network, or from the host device to the network, or both, may be either wired or wireless.

At the Poll Attached Cables state, the uploader application returns to the Wait for Devices state if no new connected product devices are found. That is, the uploader application is capable of communicating with multiple product devices that are simultaneously connected to the client device, and therefore the cable polling is with reference to checking for any new devices that were not previously detected since the time of last upload. If the Poll Attached Cables state finds a new device, then the state changes to the Check New Device state. If the Poll Attached Cables state determines that a previously connected device is now missing, then the state changes to the Check Device state.

At the Check Event state, a notification to initiate the state must have related to either a newly connected device, or a removed device. If the event related to a newly connected device, then the uploader application state is changed to the Check New Device state. If the event related to a removed device, then the uploader application state is changed to the Check Device state. If the event notification was not recognized, or if the product device was not recognized, then the uploader application returns to the Wait for Devices state.

The Check New Device state handles uploader application processing in the case of a newly connected device. If the newly connected device is recognized as a valid device for operation with the uploader application, then the state changes to the Standby Processing state (see FIG. 4). If the newly connected device is not recognized as a valid device, then the state of the uploader application returns to the Wait for Devices state. The Check Device state handles uploader application processing in the case of a missing or removed product device. If the missing or removed device is recognized as a valid device for operation with the uploader application, then the state changes to the Standby Processing state (see FIG. 4). If the missing or removed device is not recognized as a valid device, then the state of the uploader application returns to the Wait for Devices state.

If the product device is configured to communicate with the client device via a cable, then any drivers, program logic, communication protocols, and the like necessary for communication between the product device and the uploader application may be included in the cable itself. Such drivers, program logic, communication protocols, and the like necessary for communication may otherwise be provided with the product device itself, such as in the case where the client device (host device) and product device are provided in a single integrated device.

Figure 6:
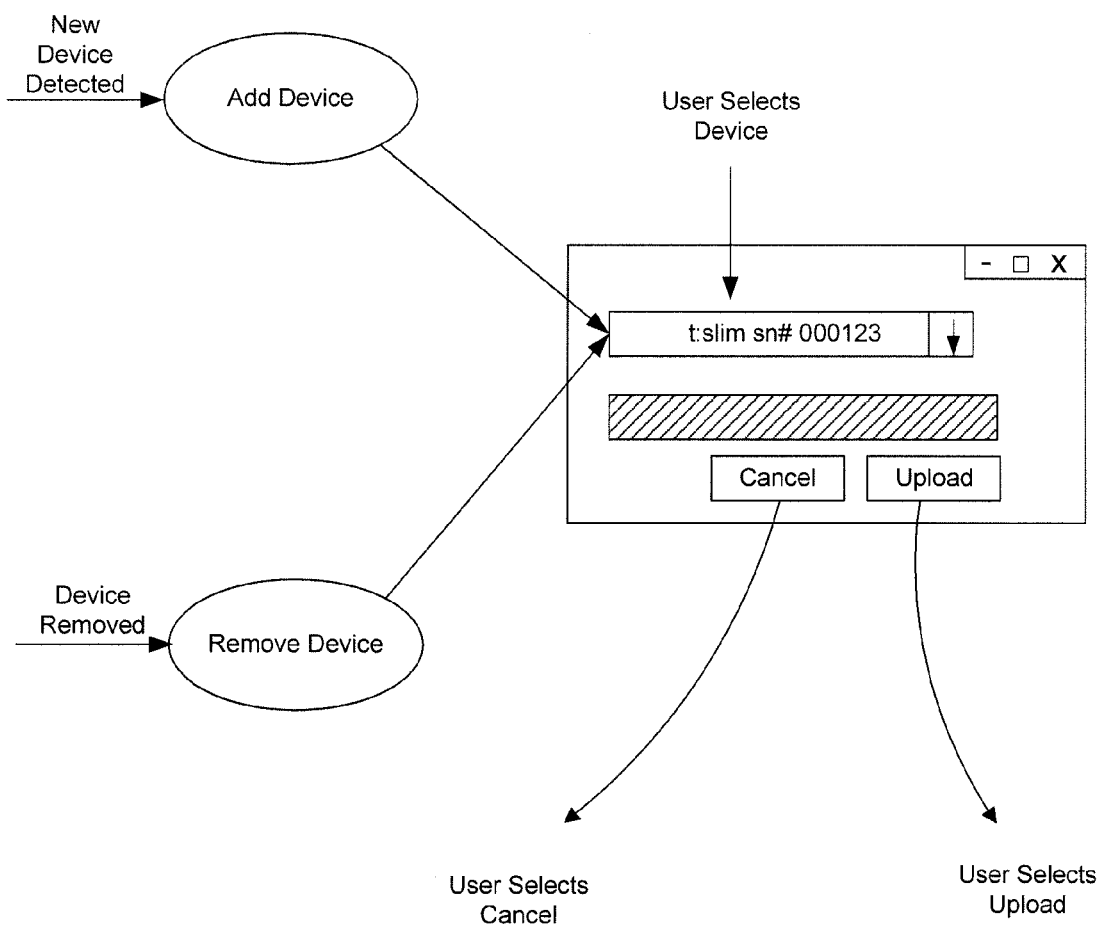
FIG. 6 is a state diagram that illustrates operation of the standby operation shown in FIG. 4.
Figure 11:
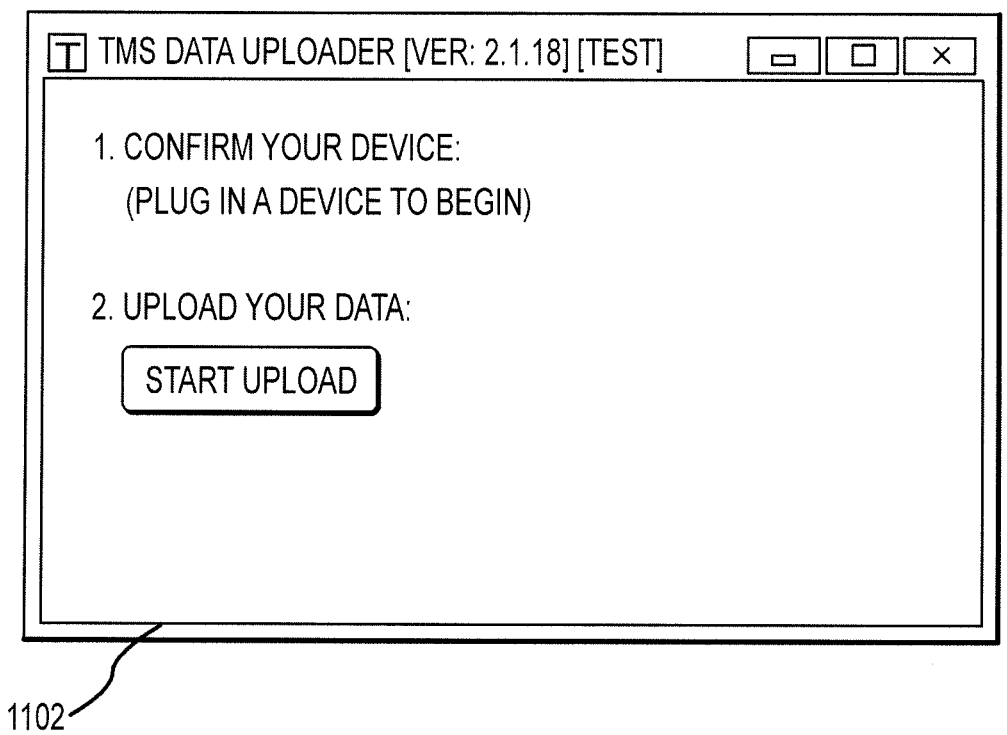
FIG. 11 is a screen shot for a computer accessing the network data manager illustrated in FIG. 1.

FIG. 6 illustrates the operation of the uploader application in the Standby Processing state shown in FIG. 4. The Standby Processing state handles processing of the uploader application while it waits for a device to be connected. An example of the display window for the uploader application, as described above, in the case of waiting for a device, is illustrated in FIG. 11. FIG. 11 shows a window 1102 with a message that indicates the user of the uploader application should connect a product device to begin operation. The "Start Upload" button in the FIG. 11 display is grayed out to indicate that the upload operation is not available, prior to detecting a supported device.

Figure 12:
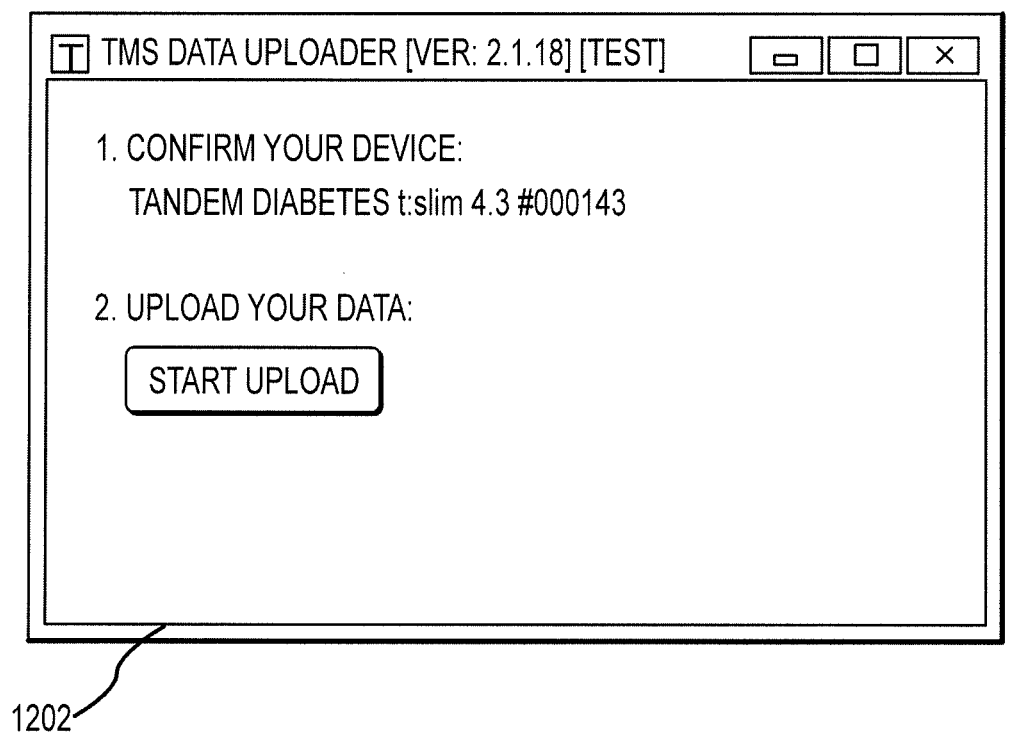
FIG. 12 is a screen shot for a computer with a single device connected while accessing the network data manager illustrated in FIG. 1.
Figure 13:
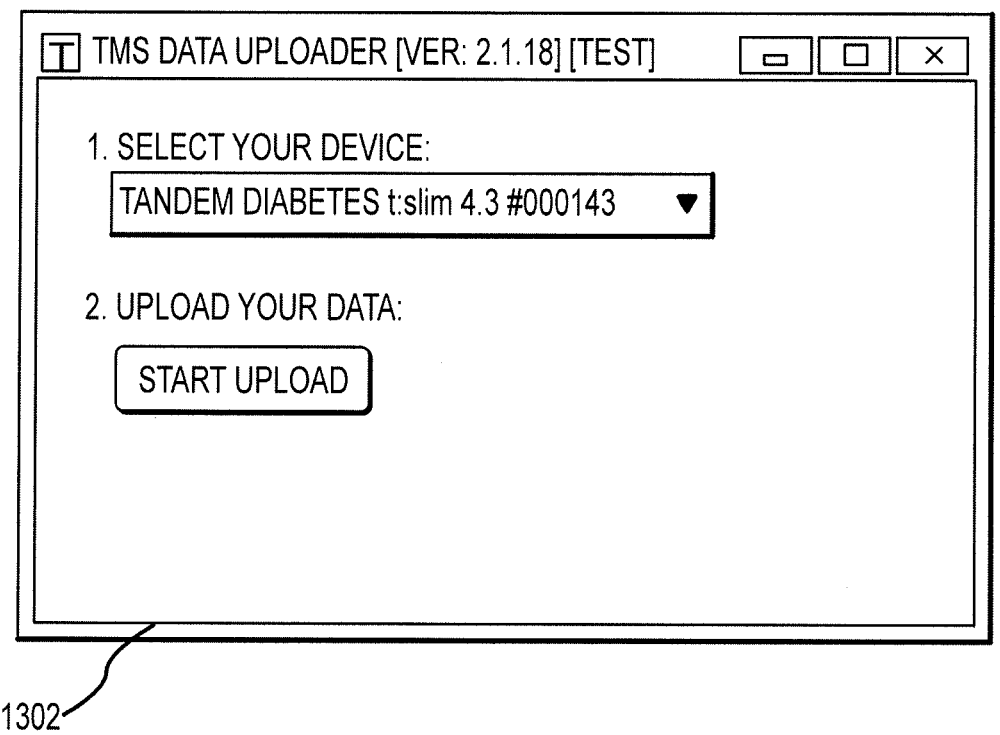
FIG. 13 is a screen shot for a computer with multiple devices connected while accessing the network data manager illustrated in FIG. 1.

In the Standby Processing state, if a supported device is detected, the display window for the uploader application is changed so that the new device is added to a drop-down menu in the display window, as indicated by the Add Device state in FIG. 6. If a single supported device is present, then a display such as illustrated in FIG. 12 is produced. FIG. 12 shows a window 1202 in which the "Start Upload" button is highlighted, to show that it can be selected by the user. If the newly connected device is a second or subsequent device to be detected, then the newly connected device is added to a drop-down menu is produced. FIG. 13 shows a window 1302 in which the device is listed, and other previously-connected devices can be viewed in a drop-down list of the window. In either case, the "Start Upload" button is available for selection by the user, to initiate upload processing. If a device is detected as removed, then the display window for the uploader application is changed so that the removed device is deleted from the drop-down menu in the display window, as indicated by the Remove Device state indicating that the GUI display is updated.

Figure 7:
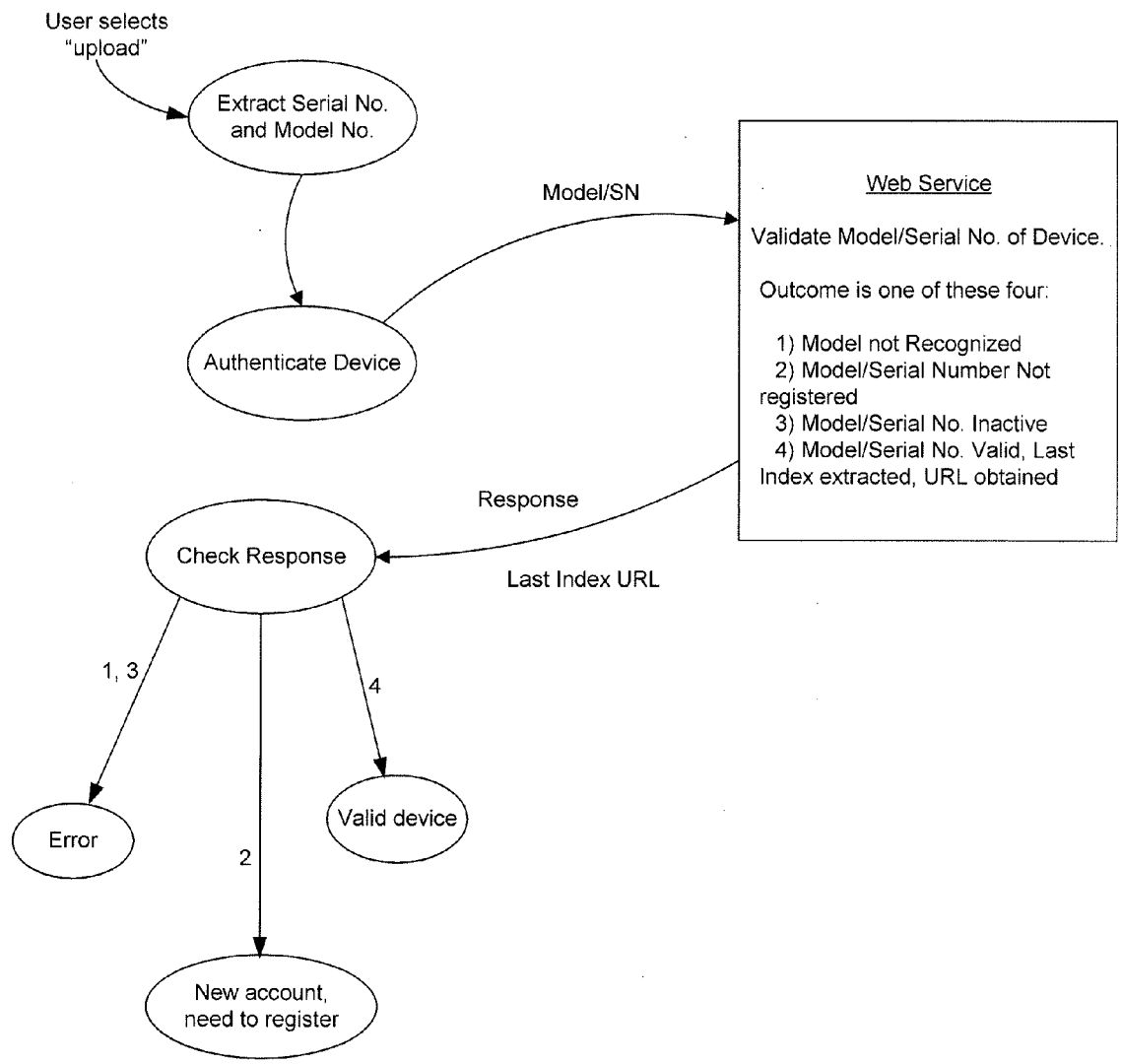
FIG. 7 is a state diagram that illustrates the authentication operation shown in FIG. 4.

FIG. 7 illustrates the operation of the uploader application in the Authenticate state shown in FIG. 4. The Authenticate state handles processing of the uploader application after the user of the uploader application has selected "Start Upload" from the GUI display. In response to the "Start Upload" selection, the uploader application state changes to the Extract Serial & Model Number state. After the requisite data is extracted, the state of the uploader application is changed to Authenticate Device, at which time the extracted data is provided to the network data manager, such as via a Web service communication. The network data manager performs the Web service and validates the extracted product device serial number and model number, as indicated by the Web Service state. The response from the network data manager, in the form of a return Web service outcome, will be one of four conditions: (1) the extracted model number was not recognized, (2) the model number and serial number were recognized, but there is no corresponding registration record, (3) the model number and serial number were recognized, but correspond to an inactive (i.e., not released or sold) product device, or (4) the model number and serial number were recognized as being associated with a valid registration, and for that registration a corresponding last uploaded index number is being returned.

At the uploader application, the response from the network data manager is checked. For authentication outcomes (1) and (3), extracted device data not recognized, an error display message is generated as the output of the Authenticate state, and the state of the uploader application changes to the Standby Processing state for display of the error message (see FIG. 4). For authentication outcome (2), extracted data recognized but no registration located, the state of the uploader application is changed to the New Account/New Device state (see FIG. 4). For authentication outcome (4), device data and registration passed, the uploader application is ready to extract the data logs from the product device, and therefore the state of the uploader application is changed to the Extract Logs state (see FIG. 4).

Figure 8:
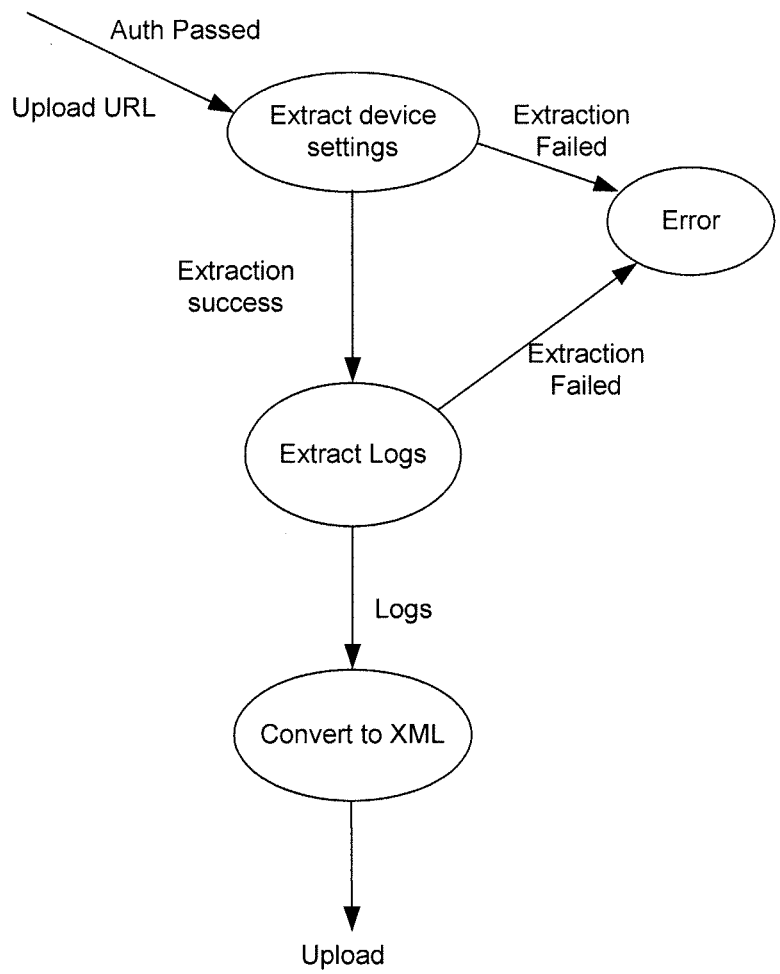
FIG. 8 is a state diagram that illustrates the extract logs operation shown in FIG. 4.

FIG. 8 illustrates the operation of the uploader application in the Extract Logs state shown in FIG. 4. The Extract Logs state handles processing of the uploader application when the most recent data logs are to be extracted from the product device and provided to the network data manager. When the uploader application receives a "passed" indication from the network data manager while in the Authenticate state, it receives a network address for a data link to be used in connection with the upload operation. For example, the network address may comprise a Uniform Resource Locater (URL) for a network location on the Internet, to which an Internet browser application of the client device may be pointed for communications. That is, the URL comprises a data link that provides access to a data storage facility. As noted above, the access via the data link is available over the computer network for a predetermined time period such that access is halted upon expiration of the predetermined time period.

In the Extract Logs state, the uploader application changes to the Extract Device Settings state and attempts to determine device settings for the product device. Such settings may comprise, as noted previously for the case of a portable insulin pump device, dosage and duration settings for the pump during daytime, such settings for the pump during night time, and the like. If such information cannot be successfully retrieved from the product device, then an error condition results, initiating an "extraction failed" data message, and the state of the uploader application is changed to an Error state before proceeding to the Standby Processing state (see FIG. 4). Similarly, the uploader application changes to the Extract Logs state and attempts to retrieve data logs from the product device. As noted above, such data logs include operational history of the device and provide a record of dosage and any difficulties in operation since the last upload event. As with the device settings, if such data log information cannot be successfully retrieved from the product device, then an error condition results, initiating an "extraction failed" data message, and the state of the uploader application is changed to an Error state before proceeding to the Standby Processing state (see FIG. 4).

If the extraction of device settings and device data logs are both successful, then the uploader application changes state to the Convert state. The Convert state involves processing the extracted data, which is typically a text string alphanumeric flat data file, to convert the extracted data into a form that is more readily usable by the network data manager and more usable by other applications and users. For example, in the exemplary embodiment, conversion of the extracted data is from a text format (e.g. ASCII) to a format such as XML (extensible markup language). Those skilled in the art will appreciate that the XML format facilitates generating data that is readily usable by a wide variety of applications. After the conversion of the extracted data, the state of the uploader application is changed to Upload (see FIG. 4).

Figure 9:
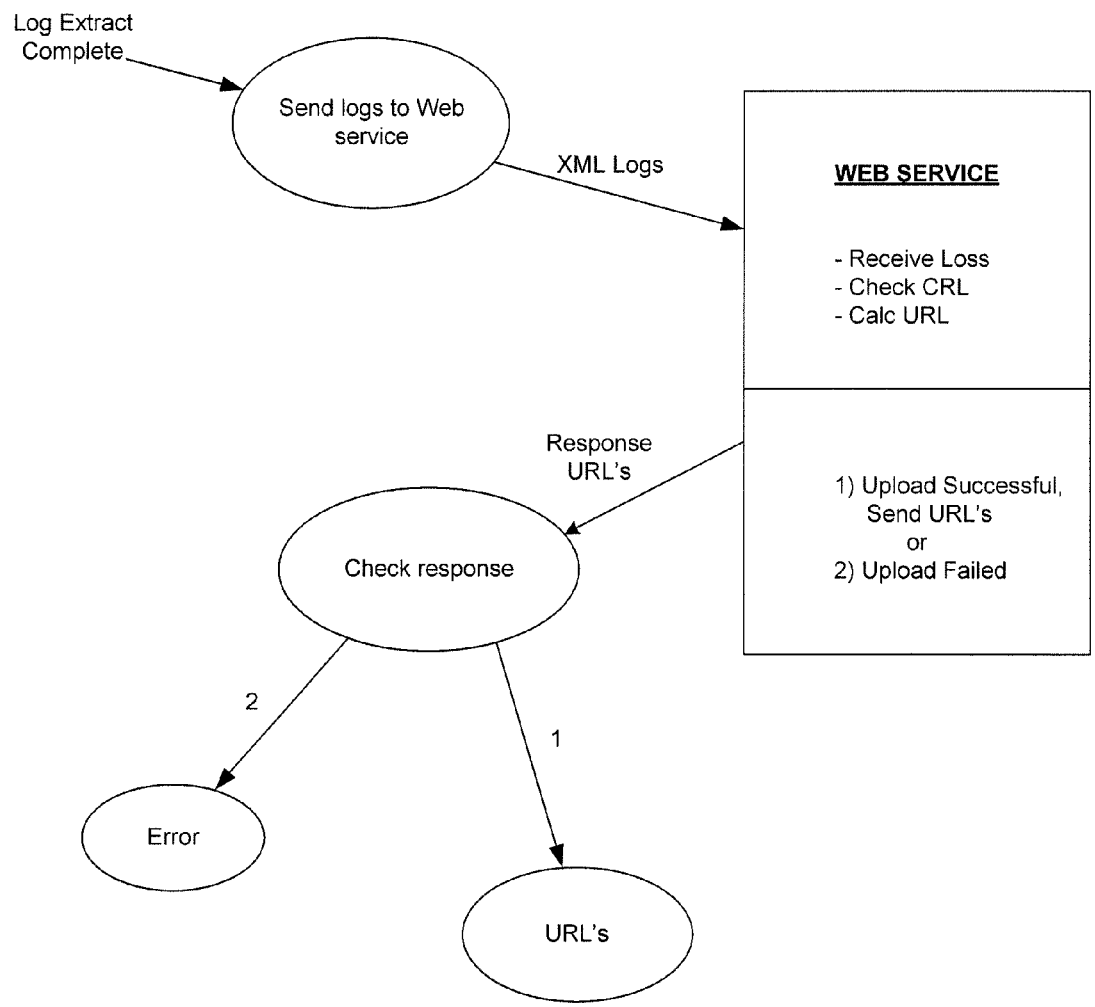
FIG. 9 is a state diagram that illustrates the upload operation shown in FIG. 4.
Figure 10:
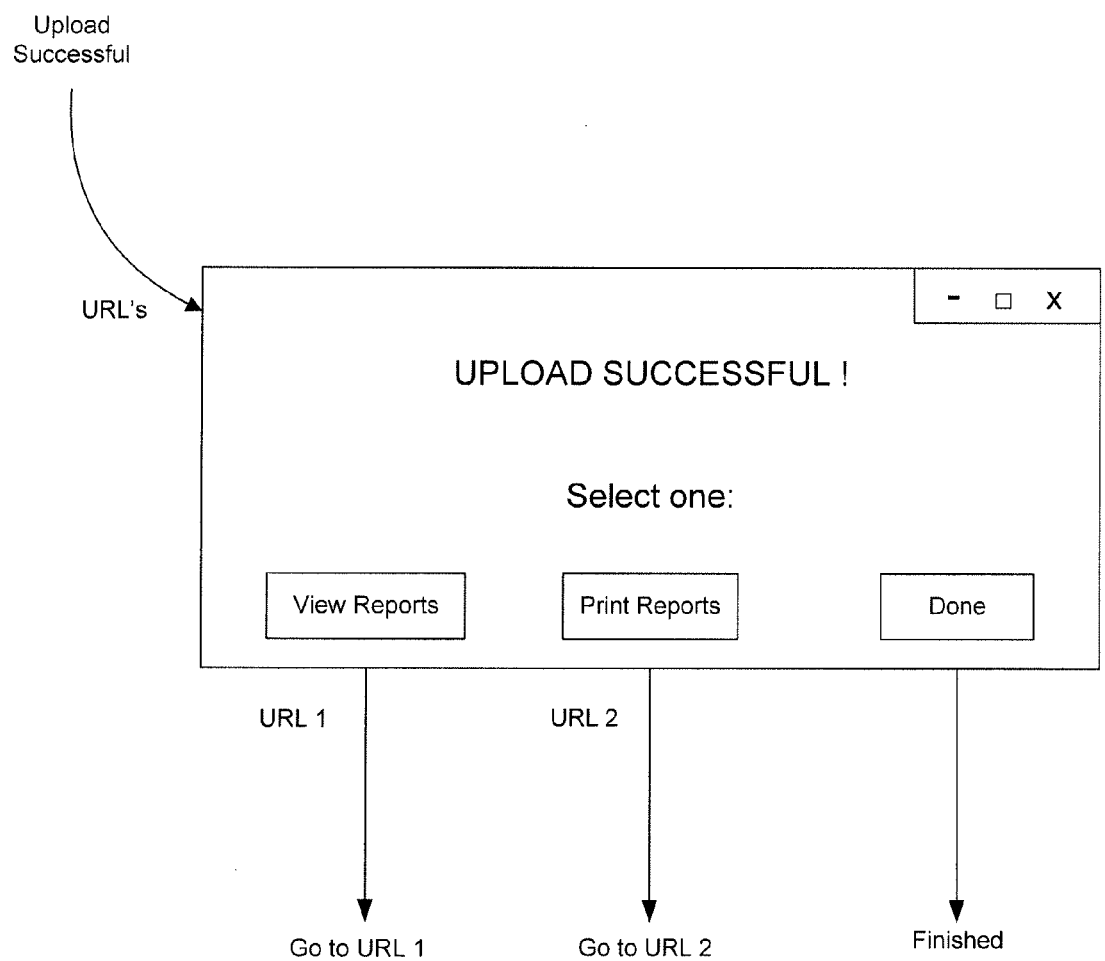
FIG. 10 is a state diagram that illustrates the Done operation shown in FIG. 4.
Figure 14:
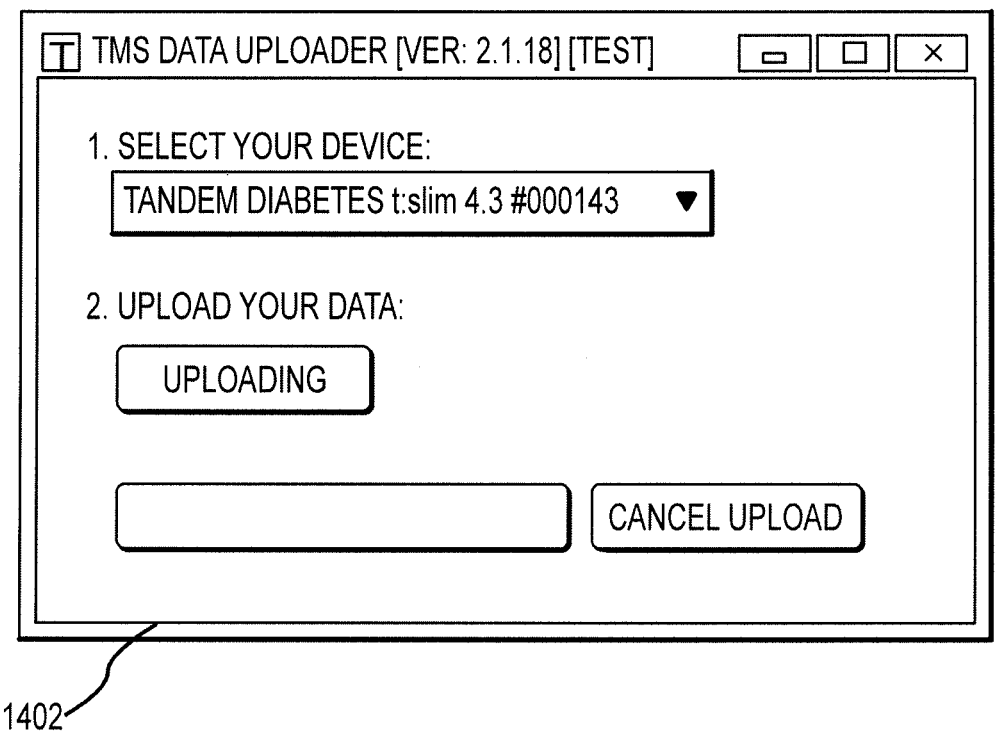
FIG. 14 is a screen shot for a computer at the start of data log uploading while accessing the network data manager illustrated in FIG. 1.

FIG. 9 illustrates the operation of the uploader application in the Upload state shown in FIG. 4. The Upload state handles processing of the uploader application for transmitting the extracted data logs to the network data manager. The initial operation in the Upload state is for the uploader application to receive an indication that the extracted data logs have been successfully retrieved from the product device, at which time the state of the uploader application changes to the Send Logs state. In that state, the uploader application sends the extracted data logs, in their converted XML format, to the Web service at the network data manager. At the network data manager, the extracted data logs are received, and any errors in the data transfer may be detected, such as through cyclic redundancy code (CRC) processing and the like, and a data link is determined for the uploader application. When the network data manager completes its processing, it sends an upload response back to the uploader application, and the uploader application changes state to the Check Response state, as indicated in FIG. 9. During operation in the Upload state, the uploader application can display a progress indication in the upload display window. An exemplary progress indication window is shown in FIG. 14, which shows the upload window 1402 with a horizontal window with a bar display for progress, and also provides a "Cancel Upload" button for the case in which the user wishes to halt the upload operation.

At the Check Response state, the response from the network data manager indicates either (1) a successful upload, or (2) a failed upload. If the upload was (1), successful, then the uploader application receives the data link and changes state to the Done state (see FIG. 4). If the upload was (2), a failure, then the uploader application receives an "upload failed" indication and the state of the uploader application changes to the Error state to produce a suitable error message and then changes to the Standby Processing state for display of the error message (see FIG. 4).

Figure 15:
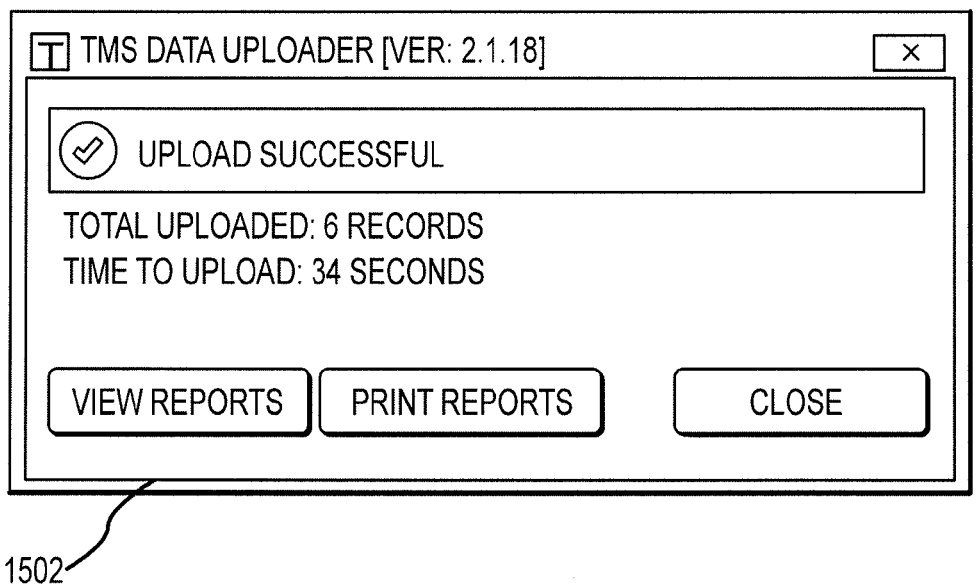
FIG. 15 is a screen shot for a computer after successful uploading to the network data manager illustrated in FIG. 1.

FIG. 9 illustrates the operation of the uploader application in the Done state shown in FIG. 4. The Done state handles processing in the uploader application for a successful operation from the Check Response state and generates an appropriate display. The display shows an "upload successful" message and waits for further user selection input. That is, the operation in the Done state provides the user with a display having options for (1) viewing a report of a data record, or (2) printing a report of a data record, or for (3) terminating operation of the uploader application. In the display window generated in the Done state, three display buttons for selecting each of the three options are provided. An exemplary display of the buttons is illustrated in FIG. 15 in an Upload Successful window 1502. If the user selects the "View Reports" button in the window, then the uploader application connects to a data link at a first URL for viewing of a data record report corresponding to the authenticated product device for which an upload was just completed. If the user selects the "Print Reports" button, then the uploader application connects to a data link at a second URL for printing of a data record report corresponding to the authenticated product device for which an upload was just completed. If the user selects the "Close" button, then the uploader application closes the network data connection and halts operation.

Figure 18:
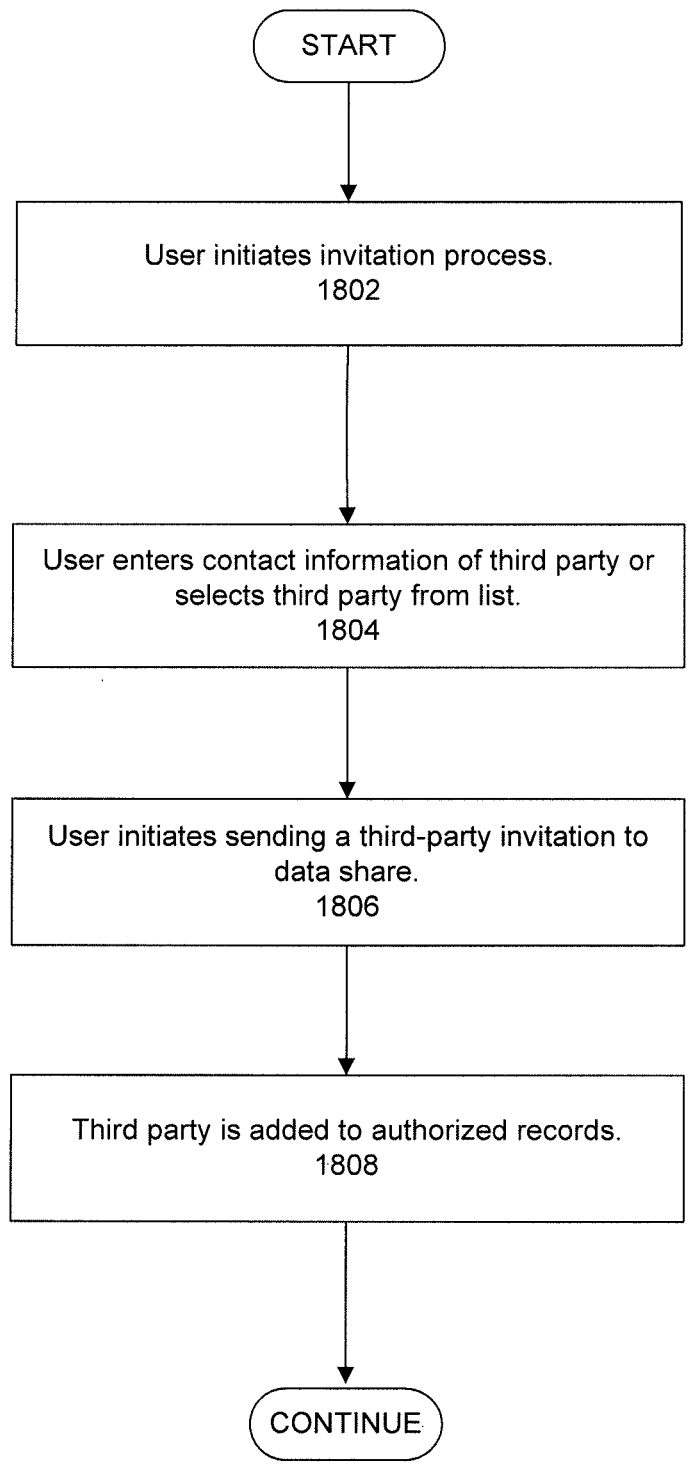
FIG. 18 is a flow diagram that illustrates operation of the system illustrated in FIG. 1 for data sharing with third parties.

As noted above, a third party may become authorized to share a user's data upon being invited by the user to share data and upon replying to the user's invitation. FIG. 18 is a flow diagram that illustrates computer operations that implement the feature.

Figure 19:
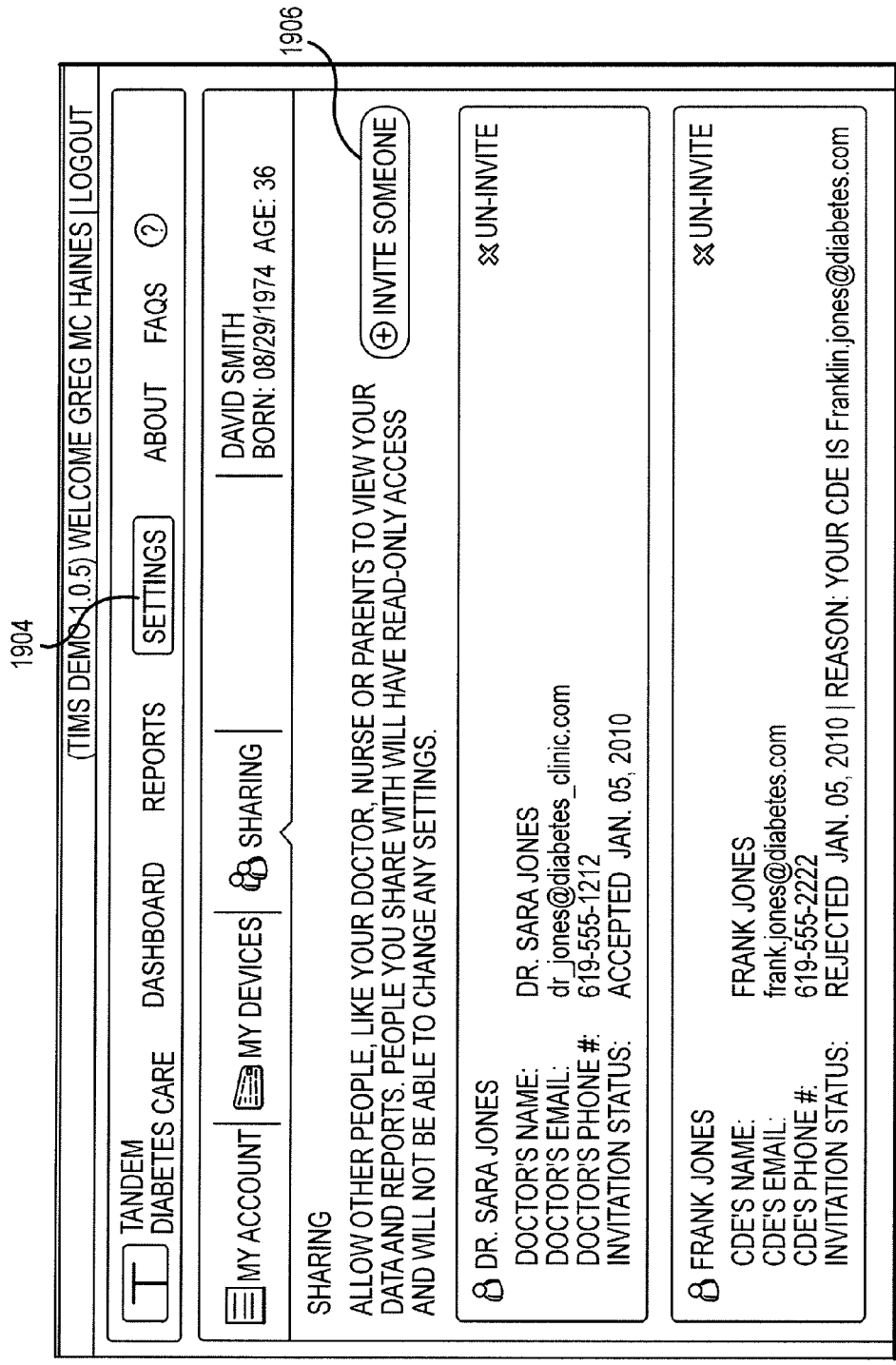
FIG. 19 is a screen shot for a computer accessing the network data manager that shows data sharing with third parties.

FIG. 18 shows operations of the exemplary embodiment in which a user initiates the invitation process by selecting an invitation process. In the illustrated embodiment, a user accesses the network data manager through a Web browser application. FIG. 19 shows a Settings window 1902 after a Sharing tab 1904 has been selected by the user to provide the user with a display button 1906 from which the user may initiate the invitation process. Third parties with whom the user has already achieved data sharing are shown in the Sharing display of FIG. 19. Although two exemplary users are illustrated, the user may implement data sharing with none, fewer, or more third parties, and the pop-up window listing would be modified accordingly. The window 1902 shows details of the respective third party invitation status and sharing information.

Figure 20:
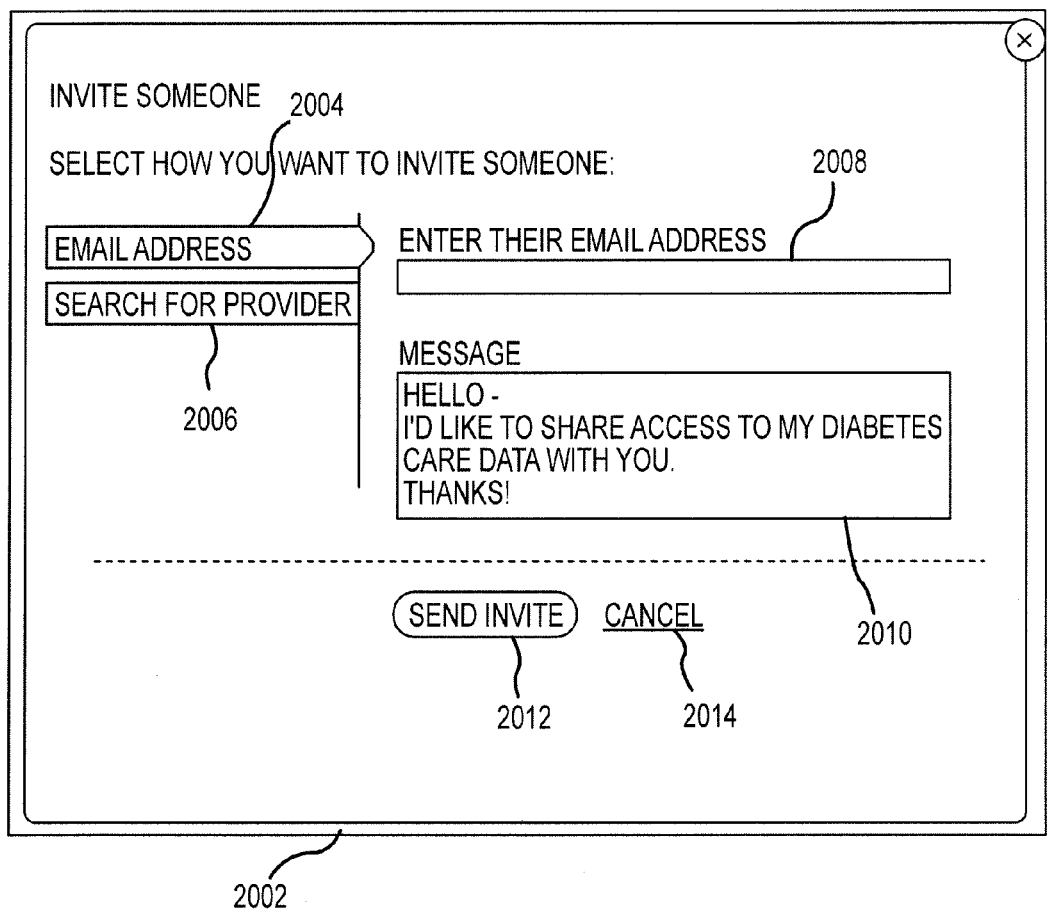
FIG. 20 is a screen shot for a computer accessing the network data manager that shows data entry of an email address for data sharing.

FIG. 20 shows an invitation pop-up window 2002 that is displayed in the user's browser after the user has selected "Invite Someone" from the display of FIG. 19. FIG. 20 shows that the user is presented with two options, to provide contact information for an invitee via a tab 2004, or to select an invitee from a data listing via a tab 2006. FIG. 20 shows details for the user to provide contact information, which is the default action in the illustrated embodiment. Thus, FIG. 20 shows a data entry box 2008 in which the user may enter contact information, such as an email address, for a third party to whom the user wishes to send an invitation for sharing data from the user's device. A message box 2010 is also provided, with text for a default message to the invitee, with the option for the user to modify the message text as desired. Upon completion of data entry, the user may select the Send Invite button 2012 to send the invitation or may use the cancel link 2014 to cancel the invitation operation.

Figure 21:
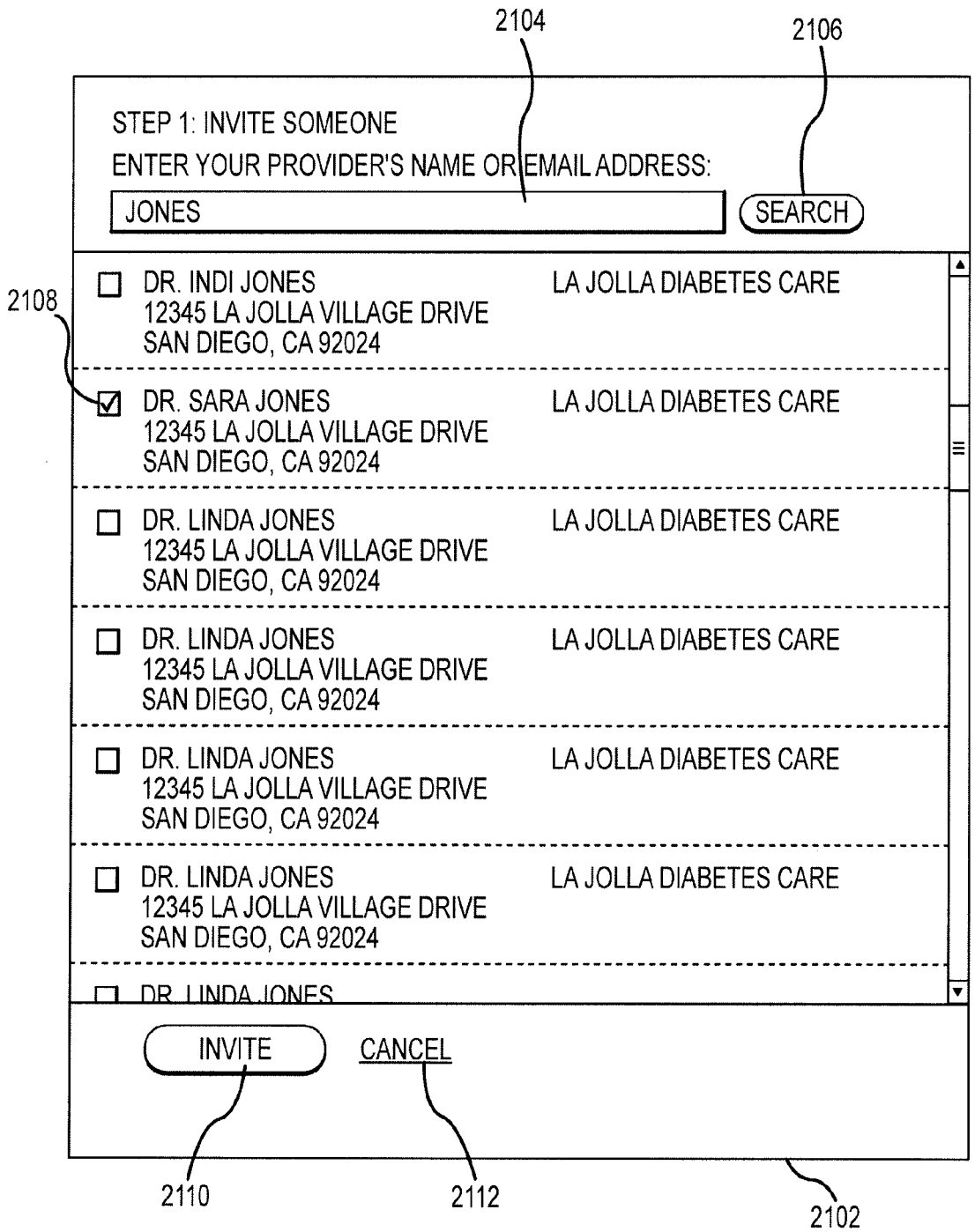
FIG. 21 is a screen shot for a computer accessing the network data manager that shows selection of a data sharing invitee from a list.
Figure 24:
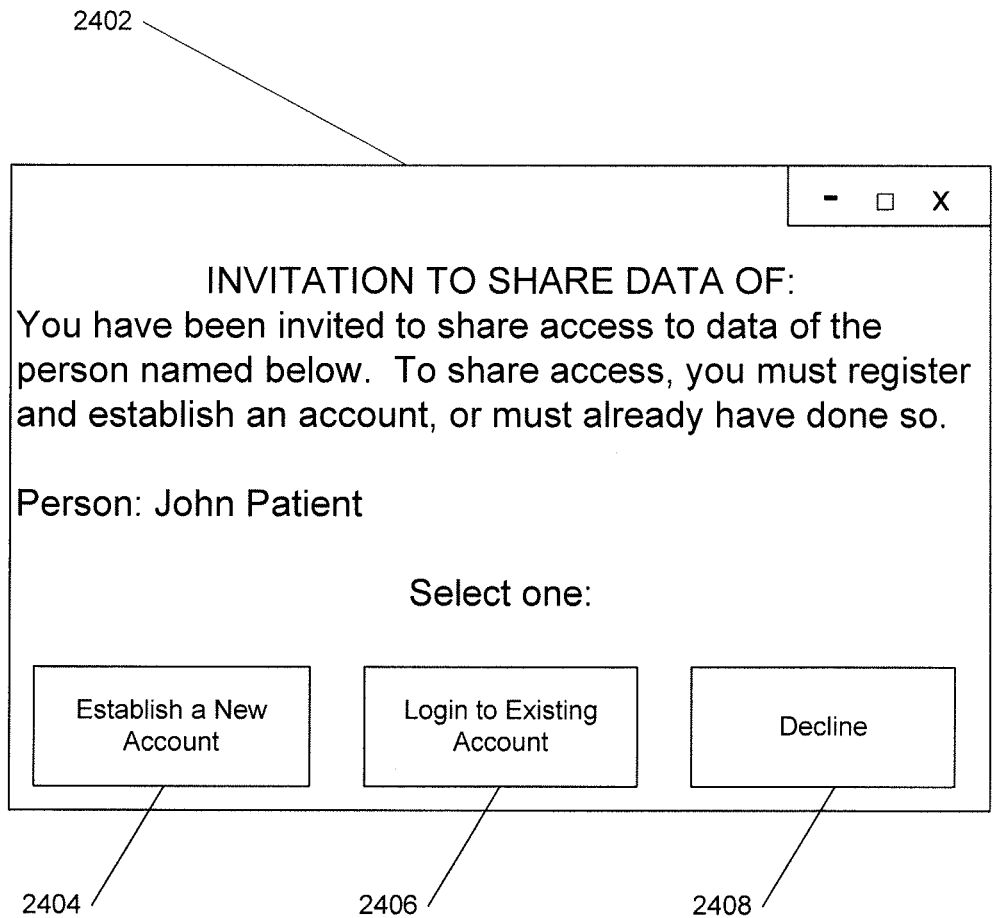
FIG. 24 is a screenshot of an invitation message sent in response to a user request to share data with a third party.

FIG. 21 shows an invitation pop-up window 2102 that is displayed in response to the user selecting "Search for Provider" tab 2006 in the default invitation pop-up window 2002 (FIG. 20). FIG. 21 shows that a list of third party providers is generated in response to selecting the search tab 2006. The list may be populated by, for example, search information inserted into a search box 2104 followed by initiating a search of available third parties by selecting a search button 2106. The available third party data over which the search is conducted may be pulled from a directory of third parties, or data from a contact list of the user or of another person or entity, or may comprise a list of registered third parties, or the like. FIG. 21 shows that the user has selected one third party by selecting a tick box 2108 corresponding to the third party. Upon completion of selecting the third party to be invited, the user may select the Send Invite button 2110 to send the invitation or may use the cancel link 2112 to cancel the invitation operation. An example of the invitation message sent by the network data manager and received by the invitee is illustrated in FIG. 24, which is a screenshot of the invitation message 2402. Upon sending the invitation from either of the windows 2002 or 2102, the third party who receives the invitation to share data may reply to the message and become authorized to share data. As noted above, the third party invitee may comprise, for example, a physician and/or an authorized member of the physician's staff, a representative from a partner device producer, a clinician, a certified diabetes educator (CDE), and the like. Upon replying to the invitation message, the invitee may be requested to provide contact information and any other data for sharing data. The invitee's data may be used to generate a data record with which the third party will be associated such that the data record includes information about the user and the user's device, thereby generating a registration record that identifies the third party as an authorized party for data sharing. The exemplary invitation message of FIG. 24 shows that a recipient may be provided with selectable display buttons that give the recipient the option to enter their data and establish a new account 2404, or may login to their account if they are already registered 2406, or may decline to proceed further 2408.

Figure 22:
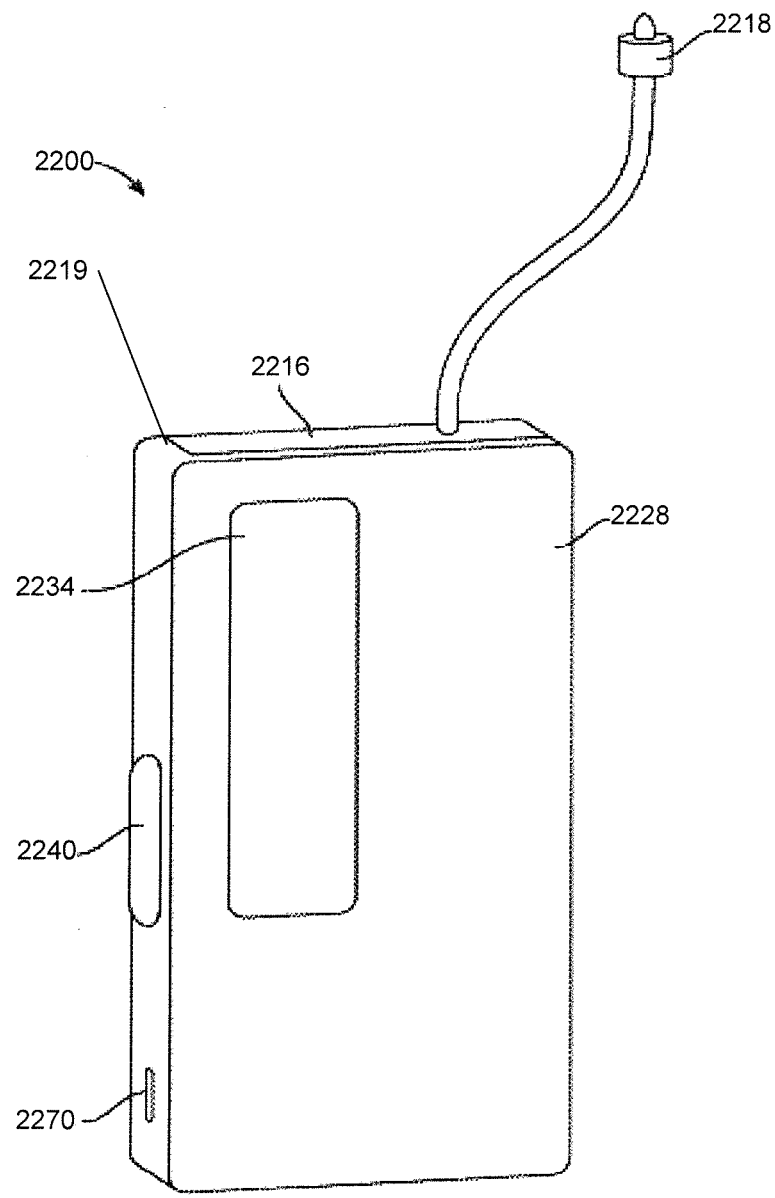
FIG. 22 is an illustration of an exemplary infusion pump device in which the features described herein are incorporated.
Figure 23:
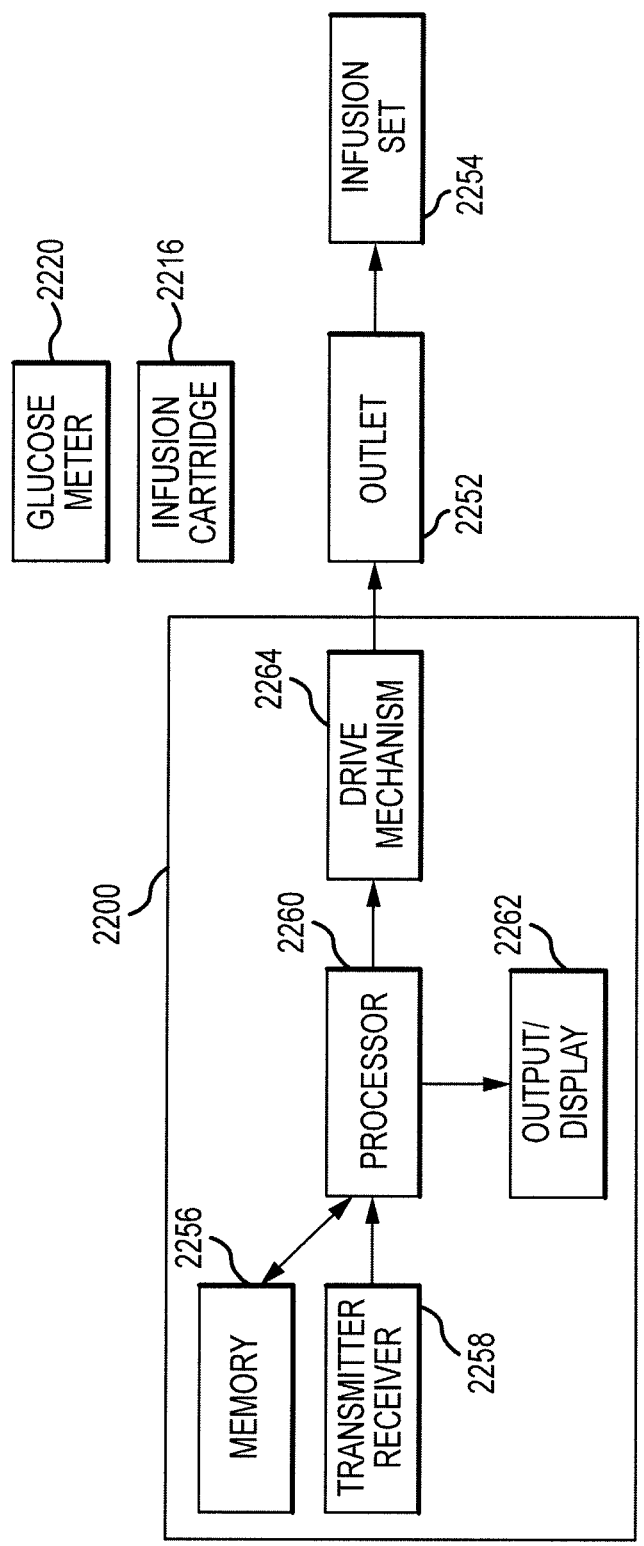
FIG. 23 is a block diagram of the device illustrated in FIG. 22.

The features described above may be implemented in a wide variety of electronic devices. One implementation, as noted above, is an embodiment comprising a portable infusion pump such as the type suitable for delivering insulin to a patient. FIGS. 22 and 23 illustrate an infusion pump device 2200 in which the features described above are incorporated. Details of constructions will be described for the infusion pump device.

FIG. 22 is an illustration of an embodiment comprising an infusion pump device 2200 that can perform the functions described herein. FIG. 23 illustrates a block diagram of the infusion pump device 2200. The infusion pump device 2200 can include an infusion cartridge 2216 having an infusion set connector 2218, and optionally a glucose meter 2220. Either the infusion cartridge 2216 or the glucose meter 2220 can be functionally and interchangeably inserted in a receiving slot 2219 of the infusion pump device. The infusion pump device 2200 can include memory 2256, transmitter/receiver 2258, processor 2260, output/display 2262, and drive mechanism 2264. The housing 2228 of the pump device 2200 can be functionally associated with an interchangeable and removable glucose meter 2220 or an infusion cartridge 2216. The infusion cartridge 2216 can have an outlet 2252 that can be connected to an infusion set connector 2218 and an infusion set 2254. The pump device may include a spool 2234 of a delivery mechanism for delivering medicaments such as insulin.

The housing 2228 of the infusion pump device 2200 can each be of any suitable shape and size. For instance, the housing 2228 may be extended and tubular, or in the shape of a square, rectangle, circle, cylinder or the like. The housing 2228 may be dimensioned so as to be comfortably associated with a user and/or hidden from view, for instance, within the clothes of a user. For some embodiments, the housing 2228 of the pump device 2200 may have a width of about 2.5 inches to about 3.5 inches, a height of about 1 inch to about 2 inches and a thickness of about 0.2 inches to about 0.6 inches. The materials of the housing 2228 may vary as well. In some embodiments, housing 2228 of the pump device 2200 may be a very water-tight, plastic housing that is glued together permanently.

The infusion pump device 2200 may include an output/display 2262. The type of output/display 2262 may vary as may be useful for particular application. The type of visual output/display may include LCD displays, LED displays, plasma displays, OLEO displays and the like. The output/display 2262 may also be an interactive or touch sensitive screen having an input device such as a touch screen, a capacitance screen, a resistive screen or the like. In some embodiments, the output/display 2244 of the pump device 2200 may be an OLEO screen or an LCD screen or a capacitance touch screen. The pump device 2200 may additionally include a keyboard or other input device known in the art for data entry, which may be separate from the display. The output/display 2262 may also include a capability to operatively couple to a secondary display device such as a laptop computer, mobile communication device such as a smartphone or personal digital assistant (PDA), or the like.

The pump device may have wired or wireless communication capability such as for the sending and receiving of data as is known in the art. The wireless capability may be used for a variety purposes, including updating of any software or firmware for the processor of the device. The wireless communication capability may vary including, e.g., a transmitter and/or receiver, radiofrequency (RF) transceiver, WIFI connection, infrared or Bluetooth® communication device. The wired communication capability may also vary including, e.g., USB or SO port, flash drive port, or the like. In some embodiments, the pump device 2200 has a network communications block such as a transmitter/receiver 2258 having a radiofrequency (RF) transceiver, that allows the pump device to communicate with other electronic devices and to be used interchangeably without loss of data or information during an infusion protocol with a single infusion cartridge 2216. Data may be transferred between the processor of the pump device and a second electronic device by radio signal, optical transmission, or any other suitable means. The pump device 2200 may be used as stand-alone device as well.

The infusion pump device 2200 may also include GPS functionality, phone functionality, warning and/or alarm programming; music storage and replay functionality, e.g., an MP3 player; a camera or video mechanism; auto scaling capabilities, and/or one or more video type games or other applications developed by third parties for use thereon. The pump device 2200 may also include an accelerometer, for instance, which may be used for changing presented estimates, wherein instead of scrolling through a menu of options or using a numerical keypad, values can be input or changed via the accelerometer, such as by gesturing with or otherwise shaking the device.

As shown in FIG. 23, the pump device 2200 has a processor 2260 that functions to control the overall functions of the device. The processor 2260 may include programming that functions to control the respective device and its components. The processor 2260 may communicate with and/or otherwise control the drive mechanism, output/display, memory, transmitter/receiver and the like. The processor of the pump device may communicate with the processor of other electronic devices, for example, through the transmitter/receiver. The processor may include programming that can be executed to control the infusion of insulin or other medicament from the cartridge, the data to be displayed by the display, the data to be transmitted via the transmitter, etc. The processor may also include programming that allows the processor to receive signals and/or other data from an input device, such as a sensor that senses pressure, temperature, and the like, that may be included as a part of the device or used in conjunction therewith. The processor 2260 may receive signals, for instance, from a transmitter/receiver on a blood glucose monitor and store the signals in the memory.

The processor 2260 may also include additional programming to allow the processor to learn user preferences and/or user characteristics and/or user history data, for instance, to implement changes in use suggestions based on detected trends, such as weight gain or loss; and may include programming that allows the device to generate reports, such as reports based upon user history, compliance, trending, and/or other such data. Additionally, pump device embodiments of the disclosure may include a "power off" or "suspend" function for suspending one or more functions of the device, such as suspending a delivery protocol, and/or for powering off the device or the delivery mechanism thereof. For some embodiments, two or more processors may be used for controller function of the pumps, including a high power controller and a low power controller used to maintain programming and pump functions in low power mode in order to save battery life.

The pump device 2200 may include a memory device 2256. The memory device 2256 may be any type of memory capable of storing data and communicating that data to one or more other components of the device, such as the processor. The memory may be one or more of a Flash memory, SRAM, ROM, DRAM, RAM, EPROM, dynamic storage, and the like. For instance, the memory may be coupled to the processor and configured to receive and store input data and/or store one or more template or generated delivery patterns. For example, the memory can be configured to store one or more personalized (e.g., user defined) delivery profiles, such as a profile based on a user's selection and/or grouping of various input factors (as described below); past generated delivery profiles; recommended delivery profiles; one or more traditional delivery profiles, e.g., square wave, dual square wave, basal and bolus rate profiles; and/or the like. The memory can also store user information, history of use, glucose measurements, compliance, an accessible calendar of events, and the like. In some embodiments, the memory 2230 of the pump device may be about 200 kB up to about 3 GB.

The pump device 2200 may include a power charging mechanism in some cases, such as a USB port, induction charger, or the like. The power charging system may be used to charge a power storage cell such as a rechargable battery of the pump device. Some embodiments may use a rechargable battery such as a NiCad battery, LiPo battery, NiMH battery or the like. In some embodiments, the power charging mechanism 2268 may be a USB port. As such, all data may be kept in the pump device for quick and easy downloading of data to a computer, other pump device, network, etc. using the USB port. The USB port may also provide the pump device 2200 with power charging. In some instances, the power charging mechanism 2268 may be an induction charging device 2270.

The uploader application described herein, as well as the network data manager and other components whose operation is described herein, may be provided as a computer program product embodied in a non-transitory computer readable storage medium containing computer implementable instructions that may be executed by a computer device. The storage medium may comprise, for example, flash memory, an optical disc such as data CD or DVD, or other computer-readable data storage device. The computer implementable instructions stored on the storage medium comprise instructions that when executed by a computer processor will provide the operation and functions described herein. The computer device for executing the enhanced media work may comprise a wide variety of computer devices that operate under control of a processor and include memory and input/output facilities, such as, for example, a mobile device or a tablet computer or a desktop or laptop computer. The mobile device may comprise, for example, a portable insulin pump device or other readily transported device that operates under control of a processor and includes memory and interfaces for input and output of data.

Some embodiments may be directed to a kit, which kit may include a device and/or a system for the transfer of device data over a computer network as described herein. Specifically, the kit may include one or more of a portable electronic device, such as an infusion device having a drive mechanism and receiving an infusion cartridge, as well as instructions for using the same, and may include an aliquot of the medicament, e.g., insulin to be delivered, as well as infusion set tubing. The instructions may be in written, audio, or pictorial form and may be included in a written manual and/or on an instruction CD or DVD, MP3 file, or accessible via a network. In certain embodiments, a training video may be included, for instance, on a separate DVD or other medium, may be accessible via a network, or may be included as programming on the portable infusion device. For instance, in certain embodiments, the portable infusion device may include a training module. The training module may be included as programming accessible by the processor of the device, wherein the software is configured to instruct a user in the proper use of the device.

It should be noted that the methods, systems, and devices discussed above are intended merely to be examples. Various embodiments may omit, substitute, or add various procedures or components as appropriate. For example, it should be appreciated that, in alternative embodiments, the methods may be performed in an order different from that described, and various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in this description to provide a thorough understanding of the embodiments. Nevertheless, it will be understood by one of ordinary skill in the art that the embodiments may be practiced without these specific details. For example, well-known circuits, processes, algorithms, structures, and techniques have been shown without unnecessary detail in order to avoid obscuring the embodiments. Further, the headings provided herein are intended merely to aid in the clarity of the descriptions of various embodiments, and should not be construed as limiting the scope of the invention or the functionality of any part of the invention. For example, certain methods or components may be implemented as part of other methods or components, even though they are described under different headings.

It is noted that embodiments may have been described as a process that is depicted as a flow diagram or block diagram. Although each diagram may describe the process as a sequential series of operations, many of the operations can be performed in parallel or concurrently. In addition, the order of the operations may be rearranged. A process may have additional steps not included in the figures.

The description above has been provided in terms of presently preferred embodiments so that an understanding of the present invention can be conveyed. There are, however, many configurations and techniques for data management systems that were not specifically described herein, but with which the present invention is applicable. The present invention should therefore not be seen as limited to the particular embodiments described herein, but rather, it should be understood that the present invention has wide applicability with respect to data management generally. All modifications, variations, or equivalent arrangements and implementations that are within the scope of the attached claims should therefore be considered within the scope of the invention.

We claim:

1. A method of providing access to data associated with a portable infusion pump over a computer network through a network data manager, the method comprising:
   receiving a request message at the network data manager from a client device to share access to data acquired by a portable infusion pump of a user and transmitted from the portable infusion pump to the network data manager with a third party medical provider, the request message including an access requestor identifier;
   determining at the network data manager that the access requestor identifier is associated with a data record that identifies the portable infusion pump;
   causing, by the network data manager, an invitation message submitted by the user to be transmitted to the third party medical provider, the invitation message including a data link through which the third party medical provider can be provided with initial authorization to have subsequent access to the data acquired by the portable infusion pump over the computer network;

in response to the third party medical provider accepting the invitation message, generating by the network data manager a registration record that identifies the third party medical provider as an authorized access partner for sharing the data acquired by the portable infusion pump via the network data manager;

receiving from the third party medical provider a request for access to the data acquired by the portable infusion pump at the network data manager;

determining at the network data manager that the third party medical provider is an authorized access partner; and providing the third party medical provider with access to the data.

2. The method of claim 1, wherein the data request comprises a request to view the data acquired by the portable infusion pump.

3. The method of claim 1, wherein the portable infusion pump is a portable insulin pump.

4. The method of claim 1, wherein the client device is integrated together into the portable infusion pump.

5. The method of claim 1, wherein the data link comprises one or more selectable objects in the invitation message.

6. The method of claim 1, wherein access partner registration data defining the third party medical provider as an authorized access partner is stored at a data storage facility.

7. The method of claim 1, wherein the data record further identifies a product user who is associated with the portable infusion pump.

8. The method of claim 7, further including:
receiving a data upload request from the client device at the network data manager;
receiving a data log containing the data associated with the portable infusion pump from the client device at the network data manager; and
storing the data log in a data storage facility.

9. The method of claim 1, further comprising:
receiving login information from the client device at the network data manager; and
identifying product user registration data that is associated with the login information and that is associated with the portable infusion pump.

10. The method of claim 9, wherein the product user registration data and/or login information are stored at a data storage facility.

11. The method of claim 1, wherein providing the third party medical provider with access to the data includes providing read-only access to device reports relating to usage of the portable infusion pump.

12. A method of providing access to stored data obtained from a portable infusion pump over a communication network through a network data manager, the method comprising:
receiving at the network data manager a request from a user to initiate an invitation process to share access to data acquired by a portable infusion pump with a third party medical provider, including data used in device reports relating to usage of the portable infusion pump;
receiving at the network data manager an identification of contact information for the third party medical provider; and
causing an invitation message submitted by the user to be transmitted to the third party medical provider using the contact information, the invitation message indicating that the user has invited the third party medical provider to share access to the data acquired by the portable infusion pump;
receiving at the network data manager a reply to the invitation message from the third party medical provider; and
providing, if the reply to the invitation message includes an acceptance of the invitation message by the third party medical provider, initial authorization to the third party medical provider to have subsequent access to the data acquired by the portable infusion pump via the network data manager, including read-only access to the device reports.

13. The method of claim 12, wherein receiving at the network data manager a request from a user to initiate an invitation process includes the request being received remotely over the communication network.

14. The method of claim 13, wherein the list of third parties is generated based on a search initiated by the user.

15. The method of claim 12, wherein receiving at the network data manager an identification of contact information for the third party medical provider includes receiving the identification by the user entering contact information for the third party medical provider.

16. The method of claim 12, wherein receiving at the network data manager an identification of contact information for the third party medical provider includes receiving the identification by the user selecting the contact information from a list of third parties.

17. The method of claim 12, further comprising receiving contact information from the third party medical provider at the network data manager.

18. The method of claim 17, wherein receiving contact information from the third party medical provider includes the third party medical provider logging into an existing account at the network data manager.

19. The method of claim 17, wherein receiving contact information from the third party medical provider includes the third party medical provider creating a new account at the network data manager.

20. The method of claim 17, wherein authorizing the third party medical provider to access the data includes generating a data record including one or more of the contact information from the third party medical provider and information regarding the user and the portable infusion pump, and wherein the data record identifies the third party medical provider as an authorized party for accessing the data.

21. The method of claim 12, wherein the invitation message includes a decline option though which the third party medical provider can decline access to the data.

22. The method of claim 12, wherein the portable infusion pump is a portable insulin pump.

23. The method of claim 12, wherein receiving at the network data manager an identification of contact information for the third party medical provider includes querying a database of registered third parties.

24. A portable infusion system for providing access to data over a communication network, the portable infusion system comprising:
a memory that stores data acquired by a portable infusion pump;
a network communications block adapted for communications with the communication network;
a processor coupled to the memory and the network communications block;
wherein the processor is configured to respond to a request from a user to initiate an invitation process to provide access to the data acquired by the portable infusion pump and stored at a network data manager by causing an invitation message submitted by the user to be transmitted to a third party medical provider indicating that the user has invited the third party medical provider to become authorized to have access to the data at the network data manager; and wherein upon receiving a reply to the invitation message from the third party medical provider including an acceptance by the third party medical provider of the invitation message, the processor is configured to store in memory data indicating that the third party medical provider is authorized to have subsequent access to the data at the network data manager.

25. The method of claim 24, wherein the processor is configured to receive the request remotely through the communication network.

26. The method of claim 24, wherein the processor is further configured to receive contact information from the third party medical provider with the reply.

27. The method of claim 26, wherein the processor receives the contact information upon the third party medical provider creating a new account accessible to the processor.

28. The method of claim 24, wherein the processor retrieves contact information from the third party medical provider logging into an existing account accessible to the processor.

29. The method of claim 24, wherein the processor is further configured to generate a data record including one or more of contact information of the third party medical provider and information regarding the user and the portable infusion pump, and wherein the data record identifies the third party medical provider as an authorized party for accessing the data.

30. The system of claim 24, wherein the processor is configured to provide read-only access to the third party medical provider to device reports relating to usage of the portable infusion pump.

* * * * *

UNITED STATES PATENT AND TRADEMARK OFFICE
CERTIFICATE OF CORRECTION

PATENT NO.         : 9,503,526 B2
APPLICATION NO.    : 13/564188
DATED              : November 22, 2016
INVENTOR(S)        : Daoud et al.

Page 1 of 2

It is certified that error appears in the above-identified patent and that said Letters Patent is hereby corrected as shown below:

On the Title Page

Item (57), Abstract, Line 5:
Delete "request or" and insert -- requestor --.

In the Specification

Column 10, Line 45:
After "between" delete "in"" and insert -- an --.

Column 19, Line 55:
After "variety" insert -- of --.

Column 20, Line 4:
After "used as" insert -- a --.

In the Claims

Claim 25, Column 25, Line 12:
Delete "method" and insert -- system --.

Claim 26, Column 25, Line 15:
Delete "method" and insert -- system --.

Claim 27, Column 25, Line 18:
Delete "method" and insert -- system --.

Signed and Sealed this
Twenty-third Day of May, 2017

Michelle K. Lee
*Director of the United States Patent and Trademark Office*

CERTIFICATE OF CORRECTION (continued)
U.S. Pat. No. 9,503,526 B2

Claim 28, Column 26, Line 3:
Delete "method" and insert -- system --.

Claim 29, Column 26, Line 7:
Delete "method" and insert -- system --.